United States Patent
Suzuki et al.

(10) Patent No.: US 7,354,746 B1
(45) Date of Patent: Apr. 8, 2008

(54) METHOD FOR PRODUCING OPTICALLY ACTIVE IHOG AND MONATIN

(75) Inventors: Shunichi Suzuki, Kawasaki (JP); Seiichi Hara, Kawasaki (JP); Toshiki Taba, Yokkaichi (JP); Yasuaki Takakura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/609,018

(22) Filed: Dec. 11, 2006

(51) Int. Cl.
*C12P 7/42* (2006.01)
*C12P 21/08* (2006.01)
*C12N 9/10* (2006.01)
*C07H 21/04* (2006.01)

(52) U.S. Cl. .................. 435/121; 435/146; 435/189; 435/193; 435/69.1; 435/252.33; 536/23.2

(58) Field of Classification Search ............... None
See application file for complete search history.

(56) References Cited

U.S. PATENT DOCUMENTS

2006/0003426 A1* 1/2006 Sugiyama et al. .......... 435/121

FOREIGN PATENT DOCUMENTS

WO    WO2006093322    *  8/2006

OTHER PUBLICATIONS

U.S. Appl. No. 11/276,614, filed Mar. 8, 2006, Suzuki et al.
U.S. Appl. No. 11/532,618, filed Sep. 18, 2006, Suzuki et al.

* cited by examiner

*Primary Examiner*—Rebecca E. Prouty
*Assistant Examiner*—Md. Younus Meah
(74) *Attorney, Agent, or Firm*—Shelly Guest Cermak; Cermak Kenealy & Vaidya LLP

(57) ABSTRACT

The present invention relates to a method for producing optically active IHOG, which can in turn be used for the production of monatin. The present invention further relates to a method for producing optically active monatin, and an aldolase which can be used in these methods. As such, the present invention enables the synthesis of 4-(Indole-3-ylmethyl)-4-hydroxy-2-oxoglutaric acid with high optical purity, which is useful as an intermediate in the synthesis of optically active monatin, from indole pyruvic acid and pyruvic acid (or oxaloacetic acid).

22 Claims, 1 Drawing Sheet

| | | |
|---|---|---|
| Consensus Sequence | 1: -XXXXXXNKXIKXXXAXXXVXXGQVSALSXXXSXXEVLGLAGFDVLVLDGEHAPNDXXTXI | 59 |
| 1. Ec_garL.gpt | 1: -MNNDVF··K·KAA·AAK·VQ····SNP·ST···········I·S·F· | 59 |
| 2. Ss(YP_312092).gpt | 1: -MNNDVF··K·KAA·AAK·VQ····SNP·ST···········I·S·F· | 59 |
| 3. Sd(YP_404806).gpt | 1: -MNNDVF··K·KAA·AAK·VQ····SNP·ST···········I·S·F· | 59 |
| 4. Sb(ZP_00698754).gpt | 1: MESLPVF··K·KAA·AAK·VQ····SNP·ST···········I·S·F· | 60 |
| 5. Se(YP_152260).gpt | 1: -MNNA·F··K·KAA·AAQ·VQ····ASP·TT···········V·S·L· | 59 |
| 6. Yf(ZP_00824544).gpt | 1: -MSLPNY··Q·RRN·QQG·TL····ANH·SA···········VT·F· | 59 |
| | | |
| Consensus Sequence | 60: PQLMALXGSXSAPVVRXPXNEPVIKRXLDIGFYNFLIPFVEXXEEAXXAVASTRYPPXG | 119 |
| 1. Ec_garL.gpt | 60: ····K·A·····V·T·········L···········TK··E·L······E· | 119 |
| 2. Ss(YP_312092).gpt | 60: ····K·A·····V·T·········L···········TK··E·Q······E· | 119 |
| 3. Sd(YP_404806).gpt | 60: ····K·A·····V·T·········L···········TK··E·Q······E· | 119 |
| 4. Sb(ZP_00698754).gpt | 61: ····K·A·····V·T·········L···········TK··E·Q······E· | 120 |
| 5. Se(YP_152260).gpt | 60: ····K·A·····V·T·········M···········TQ··A·R······E· | 119 |
| 6. Yf(ZP_00824544).gpt | 60: ····T·G·····A·C·········L···········SE··I·R······A· | 119 |
| | | |
| Consensus Sequence | 120: IRGVSVSHRXNXXGTVXDYFAXXNXNTXVQESCXGVDXDAIAAXEGVDXIFVGPXD | 179 |
| 1. Ec_garL.gpt | 120: ······A·MF···A···GS·K··L······Q···V····T····G····S· | 179 |
| 2. Ss(YP_312092).gpt | 120: ······T·MF···A···GS·K··L······Q···V····T····G····S· | 179 |
| 3. Sd(YP_404806).gpt | 120: ······A·MF···A···GS·K··L······Q···V····T····G····S· | 179 |
| 4. Sb(ZP_00698754).gpt | 121: ······A·MF···A···GS·K··L······Q···V····T····C····S· | 180 |
| 5. Se(YP_152260).gpt | 120: ······A·MF···P···GS·K··I······L···V····T····G····S· | 179 |
| 6. Yf(ZP_00824544).gpt | 120: ······G·HY···P···TI·D··M······Q···L····V····G····G· | 179 |
| | | |
| Consensus Sequence | 180: LXAALGXLGXXXPXVQXXXHFXRAXAXGKPXGLAPXADARRYLXWGATFVAVGSD | 239 |
| 1. Ec_garL.gpt | 180: A···H··NAS·D·KA·Q··N·S·H···$····E·······E········· | 239 |
| 2. Ss(YP_312092).gpt | 180: A···H··NAS·D·KA·Q··N·S·H···$····E·······E········· | 239 |
| 3. Sd(YP_404806).gpt | 180: A···H··NAS·D·KA·Q··N·S·H···$····E·······A········· | 239 |
| 4. Sb(ZP_00698754).gpt | 181: A···H··NAS·D·KA·Q··N·S·H···$····E·······E········· | 240 |
| 5. Se(YP_152260).gpt | 180: A···H··NAS·D·QT·Q··A·K·H···C····E·······E········· | 239 |
| 6. Yf(ZP_00824544).gpt | 180: S···Y··CFN·E·KV·R··D·K·Q···$····D·······E········· | 239 |
| | | |
| Consensus Sequence | 240: LGXFRXXTQXLXDXFKK | 256 |
| 1. Ec_garL.gpt | 240: ··V··SA··K··A·T·· | 256 |
| 2. Ss(YP_312092).gpt | 240: ··V··SA··K··A·T·· | 256 |
| 3. Sd(YP_404806).gpt | 240: ··V··SA··K··A·T·· | 256 |
| 4. Sb(ZP_00698754).gpt | 241: ··V··SA··K··A·T·· | 257 |
| 5. Se(YP_152260).gpt | 240: ··A··AS··K··A·T·· | 256 |
| 6. Yf(ZP_00824544).gpt | 240: ··V··SA··A··C·K·· | 256 |

METHOD FOR PRODUCING OPTICALLY ACTIVE IHOG AND MONATIN

BACKGROUND OF THE INVENTION

1. Field of the Invention

The present invention relates to a novel aldolase that produces 4-(indol-3-ylmethyl)-4-hydroxy-2-oxoglutaric acid (IHOG), which is a precursor of monatin, and methods for producing 4R-IHOG and 4R-monatin using the novel aldolase.

2. Brief Description of the Related Art 4-(Indole-3-ylmethyl)-4-hydroxy-2-glutamic acid(3-(1-amino-1,3-dicarboxy-3-hydroxy-butane-4-yl)indole (hereinafter referred to as monatin) is represented by the following structural formula. Monatin is found in the root of the plant, *Schlerochiton ilicifolius*, and because of its remarkably strong and intense sweetness, uses as a sweetener with a low caloric value are being developed (see JP-P-64-25757-A).

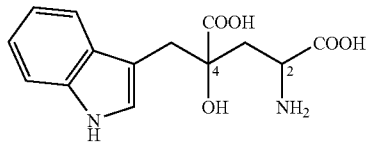

4-(Indol-3-ylmethyl)-4-hydroxy-glutamic acid

As shown in the foregoing structure, monatin has two asymmetric carbon atoms at positions 2 and 4. It has been reported that the (2S, 4S) isomer is the naturally occurring stereoisomer of monatin. Three additional stereoisomers are possible, and it has been confirmed that each of these has a sweetness intensity that is several ten to several thousand times greater than that of sucrose (Table 1).

TABLE 1

| Optical Isomer | Sweetness (vs. Sucrose) |
|---|---|
| 2R, 4R | 2700 times |
| 2R, 4S | 1300 times |
| 2S, 4R | 300 times |
| 2S, 4S | 50 times |

As is shown in Table 1, in addition to the naturally occurring (2S, 4S)-monatin isomer, the other stereoisomers have a similarly high sweetness intensity factor. Particularly, (2R, 4R)-monatin has a remarkably high sweetness intensity, which is 2,700 times greater than that of sucrose. As such, the (2R,4R) stereoisomer is particularly promising for use as a sweetening agent or as an ingredient in a sweetening agent (sweetener). Therefore, there exists a need in the art for the development of a method to efficiently produce monatin with a high content of the (2R, 4R)-monatin isomer.

To address this need, the present inventors have developed a new method for synthesizing monatin by performing the following reactions (a) and (b) using commercially available indole pyruvic acid and pyruvic acid as reagents (International Publication No. 03/056026 Pamphlet):

(a) Aldol condensation of indole pyruvic acid and pyruvic acid (or oxaloacetic acid), resulting in a keto acid (IHOG) precursor.

(b) Aminate position 2 of IHOG.

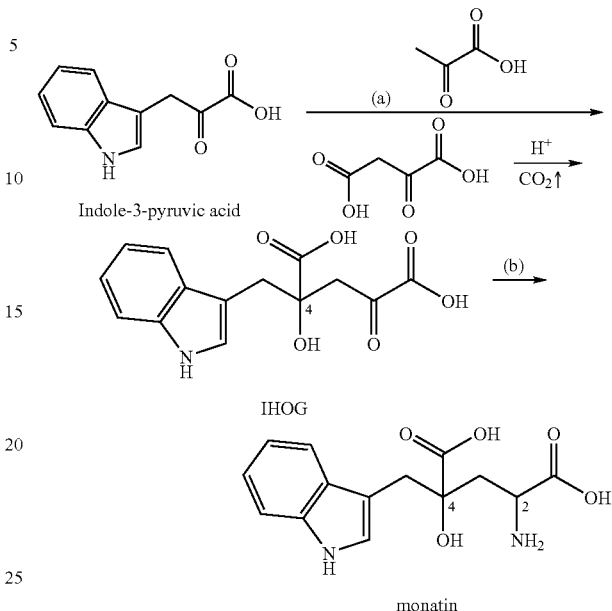

International Publication No. WO2003/056026 and 2004/018672 discloses aldolases derived from *Pseudomonas taetrolens* and *Pseudomonas coronafaciens*, and US Publication No. 2005-0244939 discloses mutant aldolases derived from the same bacteria. These enzymes are useful for producing the monatin precursor (IHOG) from indole pyruvic acid and pyruvic acid (or oxaloacetic acid) in the aldol condensation of (a). These aldolases have also been found to catalyze a reaction which produces a keto acid such as 4-phenylmethyl-4-hydroxy-2-oxoglutaric acid (PHOG), in addition to IHOG.

International Publication Nos. WO2003/091396 and WO2005/042756 discloses ProA aldolase (4-hydroxy-4-methyl-2-oxoglutarate aldolase, EC 4.1.3.17) from *Pseudomonas shafnifiea* and *Comamonas testosteroni*, KHG aldolase (4-hydroxy-2-oxoglutarate glyoxylate-lyase, EC 4.1.3.16) from *Bacillus subtilis*, *E. coli*, and *Sinorhizobium meliloti*, and so forth. In addition, International Publication No. WO2006/116487 discloses ProA from *Sinorhizobium melilotii*, KHG aldolase from *Zymomonas mobiles*, and so forth.

Furthermore, US Publication No. 2006-0003426 discloses aldolases derived from *Sphingomonas* sp. and *Burkholderia* sp. which are useful for producing the precursor keto acid (IHOG), especially 4R-IHOG, from indole pyruvic acid and pyruvic acid (or oxaloacetic acid) in the aldol condensation of (a) in the aforementioned synthesis scheme for monatin.

There are two isomers of IHOG, a 4R-isomer and 4S-isomer. In order to efficiently produce the (2R, 4R)-monatin (the isomer with highest sweetness), it is desirable to preferentially produce a 4R-isomer (4R-IHOG) (the 4S-isomer is referred to as 4S-IHOG) in the aldol condensation reaction of (a) in the aforementioned synthesis scheme of monatin, and obtain primarily the 4R-isomer of IHOG. A chiral molecule often exhibits a physiological activity that is different for each isomer, and it is also likely that each isomer of IHOG exhibits many different characteristics. Thus, 4R- and 4S-isomers which are produced separately may have uses other than as the monatin precursor. Therefore, it would be highly beneficial to develop a method for preferentially producing one isomer of IHOG (e.g., either the 4R-IHOG or 4S-IHOG).

SUMMARY OF THE INVENTION

In previous chemical synthetic systems, the IHOG which was produced was a mixture of the 4R- and 4S-isomers (racemate). Therefore, a method for efficiently producing the 4R-IHOG and 4R-monatin is still desirable in the art.

The present invention has been made in light of the above, and it is an object of the invention to provide a novel aldolase that produces PHOG and IHOG. In particular, it is an object of the present invention to provide a novel aldolase that produces 4R-IHOG, and methods for producing IHOG and monatin by the use thereof.

As a result of extensive studies to satisfy the above goal, the present inventors have found an aldolase in a certain bacterium which is suitable for the synthesis of 4R-IHOG, and by the use thereof, a method for producing 4R-IHOG and 4R-monatin is provided.

That is, the present invention includes at least the following embodiments.

It is an object of the present invention to provide a method for producing (4R)-4-(indole-3-ylmethyl)-4-hydroxy-2-oxo-glutaric acid (4R-IHOG) of formula (1), or a salt thereof:

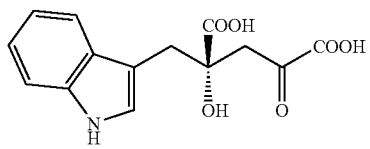

(1)

by reacting indole-3-pyruvic acid with pyruvic acid or oxaloacetic acid to produce 4R-IHOG in the presence of an aldolase,
wherein the aldolase is selected from the group consisting of:
(a) a protein comprising the amino acid sequence of SEQ ID NO:2,
(b) a protein having an amino acid sequence that contains a substitution, deletion, insertion, addition, or inversion of one or several amino acid residues in the amino acid sequence of SEQ ID No: 2 and wherein the protein has 4R-aldolase activity, and
(c) a protein that is a least 70% homologous to the amino acid sequence of SEQ ID NO:2 and wherein the protein has 4R-aldolase activity.

It is a further object of the present invention to provide a method for producing 4R-monatin or a salt thereof comprising reacting indole-3-pyruvic acid with pyruvic acid or oxaloacetic acid in the presence of an aldolase to preferentially produce 4R-IHOG or a salt thereof, wherein the aldolase is selected from the group consisting of:
(a) a protein comprising the amino acid sequence of SEQ ID NO:2,
(b) a protein having an amino acid sequence that contains a substitution, deletion, insertion, addition or inversion of one or several amino acid residues in the amino acid sequence of SEQ ID No: 2 and wherein the protein has 4R-aldolase activity,
(c) a protein that is at least 70% homologous to the amino acid sequence of SEQ ID NO:2 and wherein the protein has 4R-aldolase activity,
(d) a protein encoded by a DNA comprising the nucleic acid sequence of SEQ ID NO: 1, and
(e) a protein encoded by a DNA that hybridizes under stringent conditions with a DNA having a nucleotide sequence complementary to the nucleotide sequence of SEQ ID No: 1 and wherein the DNA encodes a protein having 4R-aldolase activity, and
converting a carbonyl group of 4R-IHOG or the salt thereof to an amino group to produce 4R-monatin, or a salt thereof, of formula (2),

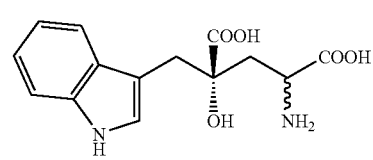

(2)

wherein a wavy line represents a bond wherein both R- and S-configurations are included.

It is a further object of the present invention to provide the method for producing 4R-monatin or the salt thereof as described above wherein said converting is by amination in the presence of an enzyme acting on 4R-IHOG.

It is a further object of the invention to provide a method for producing 4R-monatin or a salt thereof as described above wherein said converting is by a process comprising reacting 4-(indole-3-ylmethyl)-4-hydroxy-2-oxoglutaric acid contained in a reaction mixture with an amine compound or a salt thereof of formula (3):

$$H_2N-O-R \qquad (3)$$

wherein R represents a hydrogen atom, an alkyl, an aryl, or an aralkyl group, under a neutral or alkali conditions to produce 4-hydroxy-4-(3-indolylmethyl)-2-hydroxyimino-glutaric acid (IHOG-oxime) or a salt thereof of formula (4):

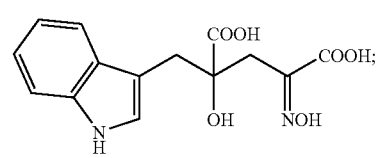

(4)

and crystallizing the 4R-isomer of the IHOG-oxime or the salt thereof; and reducing the crystallized 4R-isomer to produce 4R-monatin or the salt thereof.

It is a further object of the invention to provide the method for producing 4R-monatin as described above, wherein the amine compound of formula (3) is selected from the group consisting of hydroxylamine, methoxyamine, benzyloxyamine, and combinations thereof.

It is a further object of the invention to provide the method for producing 4R-monatin as described above wherein the 4R-isomer is reduced in the presence of hydrogen and a hydrogenated catalyst.

It is a further object of the present invention to provide the method for producing 4R-monatin or the salt thereof as described above wherein (2R, 4R)-monatin is recovered by said crystallizing.

It is a further object of the invention to provide the method for producing 4R-monatin or the salt thereof according as described above, wherein said crystallizing is performed with a crystallization solvent selected from the group consisting of water, an alcohol solvent, and an aqueous alcohol solvent.

It is a further object of the invention to provide the method for producing 4R-monatin or the salt thereof as described above, wherein the aldolase is in a form of bacterial cells or treated bacterial cells.

It is a further object of the invention to provide the method as described above, wherein the cells are modified to enhance the activity of the aldolase.

It is a further object of the invention to provide the method as described above, wherein the activity of the aldolase is enhanced by increasing the expression of the aldolase.

It is a further object of the invention to provide the method as described above, wherein the expression of the aldolase is increased by modifying an expression control sequence of the gene encoding the aldolase or by increasing the copy number of the gene encoding the aldolase.

It is a further object of the invention to provide the method as described above, wherein the gene encoding the aldolase is selected from the group consisting of:

(i) A DNA comprising the nucleic acid sequence of SEQ ID NO: 1, (ii) A DNA that hybridizes under stringent conditions with a DNA having a nucleotide sequence complementary to the nucleotide sequence of SEQ ID No: 1 and wherein the DNA encodes a protein having 4R-aldolase activity, (iii) A DNA that encodes a protein comprising the amino acid sequence of SEQ ID No: 2, (iv) A DNA that encodes a protein having an amino acid sequence that contains a substitution, deletion, insertion, addition or inversion of one or several amino acid residues in the amino acid sequence of SEQ ID No: 2 and wherein the protein has 4R-aldolase activity, and (v) A DNA that encodes a protein having an amino acid sequence that is at least 70% homologous to the amino acid sequence of SEQ ID NO: 2 and wherein the protein has aldolase activity.

It is a further object of the invention to provide the method as described above, wherein the aldolase is from a bacteria belonging to genus *Escherichia*.

It is a further object of the invention to provide the method described above, wherein the bacteria is *Escherichia coli*.

By the use of the method of the present invention, 4R-IHOG may be preferentially produced from indole pyruvic acid and pyruvic acid (or oxaloacetic acid) by using the aldolase newly cloned by the present inventors. Since 4R-monatin may be synthesized by aminating the produced 4R-IHOG, the aldolase is highly advantageous for the production of a monatin with high sweetness.

Conventionally, when the 4R-isomer is isolated from a racemic mixture of IHOG (4R, 4S-IHOG), it is necessary to oximate the racemic IHOG. The yielded 4-hydroxy-4-(3-indolylmethyl)-2-hydroxyiminoglutaric acid (IHOG-oxime) is then reacted with chiral amines to crystallize the 4R-isomer of IHOG (4R-IHOG-oxime). On the contrary, in accordance with the present invention, no optical resolution using the chiral amines is required upon crystallization because 4R-isomer-rich IHOG may be produced at the stage of aldol condensation. After the oximation, 4R-IHOG-oxime may be crystallized directly. Therefore, the purification process of 4R-IHOG is greatly simplified and shortened.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily understood by reference to the following Figures in conjunction with the detailed description below.

FIG. 1 shows a homology comparison of aldolases used in the present invention.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the food sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Furthermore, the materials, methods, and examples are illustrative only and are not intended to be limiting, unless otherwise specified.

1. General Definitions and Methods Usable for Practicing the Present Invention.

The term "bacterium" as employed in the present specification includes an enzyme-producing bacteria, a mutant and a genetic recombinant of such bacteria in which the targeted enzymatic activity exists or has been enhanced, and the like.

The phrase "increasing the expression of the gene" means that the expression of the gene is higher than that of a non-modified strain, for example, a wild-type strain. Examples of such modifications include increasing the copy number of expressed gene(s) per cell, increasing the expression level of the gene(s), and so forth. The copy number of an expressed gene is measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. The amount of the protein encoded by the gene can be measured by known methods including SDS-PAGE followed by immunoblotting assay (Western blotting analysis), and the like.

"Transformation of a bacterium with DNA encoding a protein" means introduction of the DNA into a bacterium, for example, by conventional methods. Transformation with the DNA will result in an increase in expression of the gene encoding the protein of present invention, and will enhance the activity of the protein in the bacterial cell. Methods of transformation include any known methods that have hitherto been reported. For example, a method of treating recipient cells with calcium chloride so as to increase permeability of the cells to DNA has been reported for *Escherichia coli* K-12 (Mandel, M. and Higa, A., J. Mol. Biol., 53, 159 (1970)) and may be used.

Methods of enhancing gene expression include increasing the gene copy number. Introducing a gene into a vector that is able to function in a bacterium of the present invention increases the copy number of the gene. For such purposes, multi-copy vectors are preferably used. Multi-copy vectors include pBR322, pMW119, pUC19, pET22b, pTrp4, or the like.

Enhancement of gene expression may also be achieved by introducing multiple copies of the gene into the bacterial chromosome by, for example, homologous recombination, Mu integration, or the like. For example, one Mu integration allows up to 3 copies of the gene to be introduced into the bacterial chromosome.

Increasing the copy number of the gene can also be achieved by introducing multiple copies of the gene into the chromosomal DNA of the bacterium. In order to introduce multiple copies of the gene into a bacterial chromosome, homologous recombination is carried out using a sequence which exists in multiple copies as targets in the chromosomal DNA. Sequences having multiple copies in the chromosomal DNA include, but are not limited to, repetitive DNA, or inverted repeats existing at the end of a transposable element. Also, as disclosed in U.S. Pat. No. 5,595,889, it is possible to incorporate the gene into a transposon, and allow it to be transferred into the chromosomal DNA, resulting in the introduction of multiple copies of the gene.

Enhancing gene expression may also be achieved by placing the DNA of the present invention under the control of a potent promoter. For example, the Ptac promoter, the lac promoter, the trp promoter, the trc promoter, the PR, or the PL promoter of lambda phage are all known to be potent promoters. The use of a potent promoter can be combined with increasing the gene copy number.

Alternatively, the effect of a promoter can be enhanced by, for example, introducing a mutation into the promoter to increase the transcription level of a gene located downstream of the promoter. Furthermore, it is known that substitution of several nucleotides in the spacer region between the ribosome binding site (RBS) and the start codon, especially the sequences immediately upstream of the start codon, profoundly effect the mRNA translatability. For example, a 20-fold range in expression levels was found, and was dependent on the nature of the three nucleotides preceding the start codon (Gold et al., Annu. Rev. Microbiol., 35, 365-403, 1981; Hui et al., EMBO J., 3, 623-629, 1984). Previously, it was shown that the rhtA23 mutation is an A-for-G substitution at the −1 position relative to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457).

Moreover, it is also possible to introduce a nucleotide substitution into a promoter region of the gene on the bacterial chromosome, which results in stronger promoter function. The expression control sequence can be altered, for example, in the same manner as the gene substitution using a temperature-sensitive plasmid, as disclosed in International Patent Publication WO 00/18935 and Japanese Patent Application Laid-Open No. 1-215280.

Methods for preparation of plasmid DNA include, but are not limited to, digestion and ligation of DNA, transformation, selection of an oligonucleotide as a primer and the like, or other methods well known to one skilled in the art. These methods are described, for instance, in Sambrook, J., Fritsch, E. F., and Maniatis, T., "Molecular Cloning A Laboratory Manual, Third Edition", Cold Spring Harbor Laboratory Press (2001).

The term "about" includes up to a 20% deviation from the recited value, more preferably a 10% deviation from the recited value, still more preferably a 5% deviation from the recited value, and most preferably a 2.5% deviation from the recited value.

2. Method of the Present Invention

The present invention will be described in detail in the following order:

[I] method for producing optically active IHOG, and [II] method for producing optically active monatin, with reference to the appended drawings.

[I] Method for Producing Optically Active IHOG (1) Reaction

The method for producing 4R-IHOG of the present invention involves preferentially producing 4R-IHOG represented by formula (1):

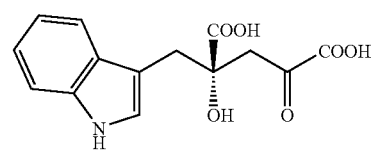

(1)

by reacting indole pyruvic acid represented by formula (5):

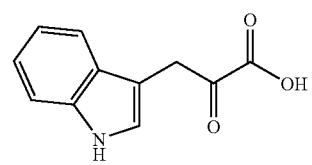

(5)

with pyruvic acid or oxaloacetic acid represented by formula (6):

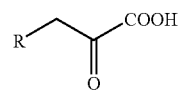

(6)

wherein R represents a hydrogen atom or a carboxyl group. The reaction above is performed in the presence of an aldolase.

The term "aldolase" preferably indicates a protein having 4R-aldolase activity, and may be obtained from a bacteria or may be chemically synthesized. The 4R-aldolase activity refers to a catalytic activity of a reaction in which 4R-IHOG represented by formula (1) is preferentially produced by aldol condensation of indole pyruvic acid of formula (5) with pyruvic acid or oxaloacetic acid represented by formula (6), and/or a reaction in which 4R-PHOG is preferentially produced from phenyl pyruvic acid and pyruvic acid.

As used herein, producing "4R-IHOG preferentially" indicates that in the method of the present invention, that the optical purity of the R-isomer is greater than that of the S-isomer at position 4, and that the optical purity of the R-isomer is preferably at least 70% and particularly preferably at least 90% of the final IHOG. Depending on reaction conditions, the optical purity value varies, but those skilled in the art may easily set the optimal conditions for the reaction. Thus, any method in which the aforementioned optical purity is obtained at around the optimal conditions is included in the present invention, even if the above optical purity has not been obtained when the reaction conditions are changed. To obtain an optical purity which is equal to or less than the above by controlling the reaction conditions for the purpose of adjusting to a desired mixture ratio of the 4R- and 4S-isomers, the protein of the present invention may be employed in the reaction. Such a case is also included in the method of the present invention. The optical purity of 4R-IHOG may be determined as an enantiomeric excess (% e.e.) by ([4R-IHOG]-[4S-IHOG])/([4R-IHOG]+[4S-IHOG])×100.

The aldolase which is described in the section entitled "(2) Aldolase" is preferable to catalyze the aforementioned reaction. Upon identifying the presence of a reaction, the aldolase may be obtained by cultivating bacterial cells that produce the protein (aldolase), which then catalyzes the reaction. Alternatively, the aldolase may be obtained by making a transformant that produces the protein that catalyzes the reaction by a recombinant DNA technique and cultivating the transformant.

The aldolase may be added to the reaction system in any form as long as the aldolase can catalyze the reaction in which 4R-IHOG is preferentially synthesized. More specifically, the aldolase may be added to the reaction system alone, or a composition having the aldolase activity comprising the protein (aldolase) may be added to the reaction system.

As used herein, the "composition having the aldolase activity" may be those containing the protein (aldolase) that catalyzes the reaction, and this term includes specifically a culture, a medium (a culture from which bacterial cells have been removed), bacterial cells (including cultured bacterial cells and washed bacterial cells), a treated bacterial cell product obtained by disrupting or lysing the bacterial cells, or a composition (crude enzyme solution, purified enzyme) having the aldolase activity obtained by purifying the medium and/or the cells. For example, when the optically active IHOG is produced using aldolase-producing bacteria or bacterial cells transformed with the recombinant DNA, a substrate may be directly added to the medium and cultivated, and the bacterial cells harvested from the medium or the washed bacterial cells may be used. Treated bacterial cells which have been obtained by disrupting or lysing the bacterial cells may be used directly, or the aldolase may be collected from the treated bacterial cell products and used as the crude enzyme solution, or furthermore a purified enzyme may be used. That is, it is possible to use a fraction having the aldolase activity in any form for the method for producing 4R-IHOG of the present invention.

To facilitate the aldol reaction using the aldolase or the composition having the aldolase activity, a reaction mixture containing indole pyruvic acid and pyruvic acid or oxaloacetic acid, and the protein that catalyzes the reaction or an aldolase-containing product may be statically incubated, shaken or stirred at an appropriate temperature of 20 to 50° C. for 30 minutes to 5 days while maintaining the pH at 6 to 12.

Herein, to produce IHOG more stereoselectively, the objective 4R-IHOG may be produced with higher stereoselectivity by suppressing spontaneous aldol condensation. IHOG produced by aldol condensation of indole-3-pyruvic acid and pyruvic acid is shown as an example (infra). In this reaction, the aldol condensation occurs spontaneously by maintaining an alkali pH, e.g., around pH 9 to 12. IHOG produced by this spontaneous aldol condensation is a mixture of the 4R- and 4S-isomers (racemate), and the stereoselectivity for the position 4 is low. Thus, in one aspect of the present invention, the pH during the reaction of the catalytic protein is controlled to pH 9 to 7, preferably around pH 8.7 to 8, so that spontaneous IHOG production is suppressed while the aldol condensation occurs selectively for the 4R-IHOG by the aforementioned catalytic protein. Consequently, the 4R selectivity of the resulting IHOG may be enhanced. Those skilled in the art may determine the reaction conditions by a simple preliminary examination.

The aldolase disclosed in the present invention is a so-called class II aldolase whose enzyme activity is increased by adding a bivalent cation. The bivalent cation added to the reaction system sometimes affects spontaneous aldol condensation, and thus, sometimes affects the stereoselectivity of position 4 in the resulting IHOG. Those skilled in the art may determine suitable conditions by simple preliminary examination depending on the type and concentration of the bivalent cation which is added to the reaction system.

The reaction rate may also be enhanced by adding a bivalent cation such as $Mg^{2+}$, $Mn^{2+}$, $Ni^{2+}$, and $Co^{2+}$ to the reaction mixture. In terms of cost, $Mg^{2+}$ is preferable. When the bivalent cation is added to the reaction mixture, any salt may be used as long as the salt does not inhibit the reaction. $MgCl_2$, $MgSO_4$, and $MnSO_4$ are preferable. Those skilled in the art may determine a preferred concentration of the bivalent cation by the simple preliminary examination. For example, when $Mg^{2+}$ is added, the spontaneous condensation rate of IHOG is suppressed by maintaining the concentration of added $Mg^{2+}$ at 1 mM or less, preferably 0.5 mM or less, and more preferably 0.1 mM or less. Consequently, the 4R selectivity of the IHOG produced via the aldolase increases.

An example of preferred reaction conditions during production of the 4R-IHOG of the present invention is shown below. 4-(Indole-3-ylmethyl)-4-hydroxy-2-oxoglutaric acid (IHOG) is obtained by adding washed bacterial cells of aldolase-expressing E. coli at 10% (w/v) to a reaction mixture composed of 100 mM buffer, 300 mM indole-3-pyruvic acid, 600 mM pyruvic acid, 0.1 mM $MgCl_2$, and 1% (v/v) toluene, and reacting with shaking at 37° C. for 4 hours.

The IHOG may be isolated and purified by generally known methods, for example, contacting IHOG with an ion exchange resin to absorb basic amino acids. The IHOG is then eluted and crystallized. An alternative method is to decolorize the eluent by filtration through active charcoal before crystallization. The reaction mixture containing the IHOG may be used directly for the next step.

In one example, the ratio of 4S-IHOG to 4R-IHOG according to the method of the present invention is about 1:7 when using GarL aldolase in the presence of 1 mM $MgCl_2$ at a pH of 9.0, and adding 300 mM indole-3-pyruvic acid and 600 mM pyruvic acid as substrates (see Example 2). Furthermore, an optical purity of at least 75% at position 4 of 4R-IHOG-oxime may be obtained by crystallizing the reaction mixture containing the 4R-IHOG after the oximation reaction, which is described later. The optical purity is the same regardless of the form, because the reaction in which IHOG is converted to IHOG-oxime using hydroxylamine has no optical selectivity for position 4.

4R-IHOG obtained in this manner is highly useful as an intermediate for the production of 4R-monatin.

(2) Aldolase

The aldolase used in the method of the present invention is able to catalyze the aforementioned reaction.

(i) DNA which Encodes the Aldolase

There are several aldolases found in *E. Coli*, and all are biosynthetic enzymes which are encoded by different genes. Among these, the present inventors have isolated the aldolase gene garL from *E. Coli* strain JM109, and have confirmed that garL encodes an aldolase which is able to catalyze production of 4R-IHOG from indole pyruvic acid and pyruvic acid (or oxaloacetic acid).

The garL gene has been previously reported (GeneBank accession no. AAC76160) (SEQ ID NO: 1), and is located between the garP and garR genes on the chromosome of *E. Coli* strain K-12. The nucleotide sequence of the garL gene and the encoded amino acid sequence of the GarL protein (hereinafter also referred to as "GarL aldolase") are shown in SEQ ID NO: 1 and SEQ ID NO: 2, respectively.

GarL aldolase belongs to the family of alpha-dehydro-beta-deoxy-D-glucarate aldolases (EC4. 1. 2. 20).

In addition to the garL gene from *E. coli*, genes encoding this aldolase from other microorganisms can be identified by homology to the known genes encoding aldolases, followed by evaluation of the activity of encoded proteins. To confirm aldolase activity, methods described in the following section "(3)(i) Screening method for bacteria having 4R-aldolase activity" can be used to evaluate such genes in the expressed form.

Homology between two amino acid sequences can be determined using well-known methods, for example, the computer program BLAST 2.0, which calculates three parameters: score, identity, and similarity.

Therefore, the garL gene or any homologs thereof can be obtained by PCR (polymerase chain reaction; refer to White, T. J. et al., Trends Genet., 5, 185 (1989)) utilizing primers based on the known nucleotide sequence of the gene. Genes encoding the aldolase from other microorganisms can be obtained in a similar manner.

Of these, DNA encoding an aldolase usable in the present invention is not limited to the DNA shown in SEQ ID NO:1, because differences in nucleotide sequence are observed among different species.

That is, the DNA encodes a protein which is at least 70% homologous, preferably at least 80% homologous, more preferably at least 90% homologous, still more preferably at least 95% homologous, and particularly preferably at least 98% homologous to the amino acid sequence of SEQ ID NO:2, and wherein the encoded protein also has aldolase activity, preferably 4R-aldolase activity. Examples of homologous proteins which are 90% or more homologous to the GarL aldolase include, but are not limited to, protein Z4478 (Accession No. NP_289697), 2-dehydro-3-deoxyglucarate aldolase (Accession No. NP_755748), and 2-dehydro-3-deoxyglucarate aldolase (PDB Accession No. 1DXF) from *E. coli*; protein SSO_3281 (Accession No. YP_312092) from *Shigella sonnei*; protein SDY_3320 (Accession No. YP_404806) from *Shigella dysenteriae*; 2,4-dihydroxyhept-2-ene-1,7-dioic acid aldolase (Accession No. ZP_00698754) from *Shigella boydiiand*; 5-keto-4-deoxy-D-glucarate aldolase (Accession No. YP_152260, NP_457635) from *Salmonella enterica*; and 2,4-dihydroxyhept-2-ene-1,7-dioic acid aldolase (Accession No. ZP_00824544) from *Yersinia mollaretii*. Homology comparison among these proteins and GarL aldolase is shown in FIG. 1. A consensus sequence (SEQ ID NO:5) of the aldolases is shown in the upper lane in FIG. 1. 188 of the amino acid residues are conserved, which is 73% of the total residues. The homology between GarL aldolase and the protein Z4478 (Accession No. NP_289697) is 99.6%; the homology between GarL aldolase and the 2-dehydro-3-deoxyglucarate aldolase (Accession No. NP_755748), protein SSO_3281 (Accession No. YP_312092), protein SDY_3320 (Accession No. YP_404806), 2,4-dihydroxyhept-2-ene-1,7-dioic acid aldolase (Accession No. ZP_00698754), or 2-dehydro-3-deoxyglucarate aldolase (Accession No. 1DXF) is 99.2%; the homology between GarL aldolase and 5-keto-4-deoxy-D-glucarate aldolase (Accession No. YP_152260 or NP_457635) is 91.0% or 90.6%; and the homology between GarL aldolase and 2,4-dihydroxyhept-2-ene-1,7-dioic acid aldolase (Accession No. ZP_00824544) is 80.1%.

The terms "homology (homologous)" and "identity (identical)" are interchangeable in the present specification, and therefore have the same meaning. The homology was analyzed using gene analysis software "Genetyx ver. 7" (Genetyx Corporation), and values were calculated using default parameters.

The DNA of the present invention are not limited to the DNA encoding the isolated aldolase, and of course, even if the DNA encoding the aldolase isolated from the chromosomal DNA of the aldolase-producing bacteria is artificially mutated, if the DNA encodes an active aldolase, this DNA is encompassed by the present invention. A common and frequently used method to produce an artificial mutation is site-directed mutagenesis (Method in Enzymol., 154 (1987)).

DNA which hybridizes with a nucleotide sequence which is complementary to the nucleotide sequence of SEQ ID NO:1 under stringent conditions, and encodes a protein having aldolase activity, preferably the 4R-aldolase activity, is also included in the present invention.

As used herein, the term "stringent conditions" refers to conditions where a so-called specific hybrid is formed and a non-specific hybrid is not formed. Examples thereof may include conditions where a pair of DNA sequences with high homology, e.g., DNA sequences having a homology of at least 75%, more preferably at least 80%, still more preferably at least 90% homology and particularly preferably at least 95% homology, hybridize whereas DNA with lower homology do not hybridize, and washing conditions typical of Southern hybridization, i.e., hybridization at salt concentrations equivalent to 0.1×SSC and 0.1% SDS at 37° C., preferably 0.1×SSC and 0.1% SDS at 60° C., and more preferably 0.1×SSC and 0.1 SDS at 65° C.

Herein, the "aldolase activity" or the "4R-aldolase activity" is the same as defined in the following section (ii) Aldolase. But, when the nucleotide sequence hybridizes with the complementary nucleotide sequence of SEQ ID NO:1 under stringent conditions, the expressed protein should retain aldolase activity, preferably the 4R-aldolase activity, of at least 10%, preferably at least 30%, more preferably at least 50%, and still more preferably at least 70% as compared to aldolase activity of the protein of SEQ ID NO:2 under conditions of 33° C. at pH 9.

Additionally, a DNA molecule encoding the substantially the same protein as the aldolase encoded by the DNA of SEQ ID NO:1 is also encompassed by present invention. That is, (i) a DNA having the nucleic acid sequence of SEQ ID NO: 1, (ii) a DNA that hybridizes under stringent conditions with a DNA having a nucleotide sequence complementary to the nucleotide sequence of SEQ ID No: 1, and wherein the DNA encodes a protein having 4R-aldolase activity, (iii) a DNA that encodes a protein having the amino acid sequence of SEQ ID No: 2, (iv) a DNA that encodes a protein having an amino acid sequence that contains a substitution, deletion, insertion, addition, or inversion of one or several amino acid residues in the amino acid sequence of SEQ ID No: 2, and wherein the protein has 4R-aldolase activity, and (v) a DNA that encodes a protein having an amino acid sequence that is at least 75% homologous, preferably at least 80% homologous, more preferably at least 90% homologous, still more preferably at least 95% and particularly preferably at least 98% homologous to the amino acid sequence of SEQ ID NO: 2, and wherein the protein has aldolase activity, are also encompassed by the present invention.

Herein, the significance of "one or more" is the same as that defined in the following section (ii) Aldolase.

(ii) Aldolase

As explained above, the aldolase of the present invention is preferably encoded by garL.

Any protein which has at least 70% homology, preferably at least 80% homology, still preferably at least 90% homology, still more preferably at least 95% homology, and particularly preferably at least 98% homology to the amino acid sequence of SEQ ID NO:2 and has similar enzyme activity is also encompassed by the present invention. A protein having at least 70% homology to the amino acid sequence of SEQ ID NO:2 and having the consensus sequence of SEQ ID NO:5 is particularly preferred.

Examples of such homologous proteins are the same as exemplified in the above section (i).

Therefore, the protein which has the 4R-aldolase activity includes the aldolase of the present invention, as well as the following proteins:

(a) a protein having the amino acid sequence of SEQ ID NO:2, (b) a protein having an amino acid sequence that contains a substitution, deletion, insertion, addition or inversion of one or several amino acid residues in the amino acid sequence of SEQ ID No: 2, and wherein the protein has 4R-aldolase activity, (c) a protein that is at least 70% homologous, preferably at least 80% homologous, more preferably at least 90% homologous, still more preferably at least 95%, and particularly preferably at least 98% homologous to the amino acid sequence in SEQ ID NO:2, and wherein the protein has 4R-aldolase activity, (d) a protein encoded by a DNA having the nucleic acid sequence of SEQ ID NO: 1, and (e) a protein encoded by a DNA that hybridizes under stringent conditions with a DNA having a nucleotide sequence complementary to the nucleotide sequence of SEQ ID No: 1, and wherein the DNA encodes a protein having 4R-aldolase activity.

As used herein, "one or several amino acids" indicates a range of amino acid changes or mutations which do not significantly impair the three dimensional structure of the protein nor the aldolase activity, and specifically includes from 1 to 75, preferably 1 to 50, more preferably 1 to 25, still more preferably 1 to 13, and particularly preferably 1 to 5 amino acid residues. But it is desirable that the protein having the amino acid sequence comprising one or several substituted, deleted, inserted, added, or inverted amino acid residues in the amino acid sequence of SEQ ID NO:2 retains not less than 10%, preferably not less than 30%, more preferably not less than 50% and still more preferably not less than 70% of the aldolase activity, preferably the 4R-aldolase activity, as compared to the aldolase activity of the protein having the amino acid sequence of SEQ ID NO:2 at 33° C. and pH 9.

The above "substitution, deletion, insertion, addition, or inversion" includes conservative mutation(s), so that the aldolase activity is retained. The conservative mutation is typically a conservative substitution. Substitution of amino acids regarded as the conservative substitutions include the substitution of Ala with Ser or Thr, the substitution of Arg with Gln, His or Lys, the substitution of Asn with Glu, Gln, Lys, His or Asp, the substitution of Asp with Asn, Glu or Gln, the substitution of Cys with Ser or Ala, the substitution of Gln with Asn, Glu, Lys, His, Asp or Arg, the substitution of Glu with Asn, Gln, Lys or Asp, the substitution of Gly with Pro, the substitution of His with Asn, Lys, Gln, Arg or Tyr, the substitution of Ile with Leu, Met, Val or Phe, the substitution of Leu with Ile, Met, Val or Phe, the substitution of Lys with Asn, Glu, Gln, His or Arg, the substitution of Met with Ile, Leu, Val or Phe, the substitution of Phe with Trp, Tyr, Met, Ile or Leu, the substitution of Ser with Thr or Ala, the substitution of Thr with Ser or Ala, the substitution of Trp with Phe or Tyr, the substitution of Tyr with His, Phe or Trp and the substitution of Val with Met, Ile, or Leu.

In the following context, the term "aldolase activity" indicates the 4R-aldolase activity, and is the activity that can catalyze the reaction in which 4R-IHOG is preferentially produced by the aldol condensation of indole pyruvic acid and pyruvic acid or oxaloacetic acid as described in the above section (1) Reaction. As used herein, producing "4R-IHOG preferentially" indicates that the optical purity for the R-isomer is greater than that for the S-isomer at position 4 of the produced IHOG, and preferably indicates that the R-isomer is efficiently produced at the optical purity of at least 70%, and particularly preferably at least 90%.

(3) Method for Producing Aldolase

Preferred methods for producing the aldolase will now be described. The aldolase may be produced by cultivating an aldolase-producing microorganism, and/or an aldolase-producing transformant can be made by recombinant DNA technology and cultured.

(i) Screening Method for Bacteria Having 4R-Aldolase Activity

The bacterium having 4R-aldolase activity may be obtained from the natural environment such as soil and water. That is, it is desirable to add the substrate of the objective aldolase, for example, monatin, IHOG, IHOG-oxime, PHG, PHOG, or PHOG-oxime, into the medium, and inoculate the bacterial source, followed by cultivation. It is preferable that the aldolase substrate is the source of carbon or nitrogen in the cultivation, and preferably is the sole carbon or nitrogen source. The substrate additive may be a racemic mixture, but is preferably the 4R-isomer, and is more preferably (2R, 4R)-monatin. Organic nutrients other than the above-mentioned carbon source may be appropriately selected from typical medium ingredients. Examples of nitrogen sources include, an ammonium salt of an organic acid, a nitrate salt, and organic nitrogen compounds such as peptone, yeast extract, and meat extract, or mixtures thereof. Additionally, typical nutrients, such as inorganic salts, trace metals and vitamins, may be appropriately mixed. The bacterium capable of growing in such an enriched cultivation environment abundantly contains aldolase active bacteria.

Subsequently, a single colony is obtained from enriched bacterium in the aforementioned medium, and the colony is regrown on a cultivation plate using the objective substrate as the sole source of carbon, and the aldolase activity thereof is evaluated. Other than the carbon source indication, typical cultivation conditions may be used. Examples thereof include those described in (c) "Method for culturing bacterium having aldolase activity" (infra).

To evaluate the aldolase activity produced by the bacterium, it is desirable to purify the enzyme from the bacterial cells and evaluate the enzymatic reaction using the purified enzyme. Specific examples include i) detecting liberated pyruvic acid from IHOG or PHOG as the substrate (degradation activity detection), and ii) detecting IHOG or PHOG produced by the aldol condensation using indole pyruvic acid or phenyl pyruvic acid and pyruvic acid (or oxaloacetic acid) as the substrates by high performance liquid chromatography (HPLC) measurement (synthetic activity detection). Furthermore, the 4R selectivity can be evaluated by determining the molecular asymmetry at position 4 in IHOG or PHOG produced by the aldol condensation in ii) using HPLC.

Specifically, the aldolase activity may be determined by adding the aldolase to a reaction mixture containing 100 mM buffer, 300 mM indole-3-pyruvic acid, 600 mM pyruvic acid, 0.1 mM $MgCl_2$ and 1% (v/v) toluene, reacting with shaking at 37° C. for 4 hours, and quantifying the amount of IHOG by HPLC.

IHOG may be analyzed quantitatively by HPLC equipped with, for example, "Inertsil ODS-2" (5 μm, 4.6×250 mm) supplied from GL Sciences Inc. One example of analysis conditions is shown below.

Mobile phase: 40% (v/v) acetonitrile/5 mM tetrabutylammonium dihydrogen phosphate solution Flow rate: 1 mL/min Column temperature: 40° C.

Detection: UV 210 nm (ii) Process by Recombinant DNA Technology

Numerous examples have been reported for producing useful proteins, such as enzymes and physiologically active substances, by taking advantage of recombinant DNA technology. By the use of the recombinant DNA technology, it is possible to produce large amounts of a useful protein that is naturally present in trace amounts. General methods as described in the above section "1. General definitions and methods usable for practicing the present invention" can be also used.

First, a DNA molecule encoding the aldolase of the present invention is prepared. Then, the prepared DNA molecule is ligated to a vector DNA to make a recombinant DNA, and cells are transformed with the recombinant DNA to make transformants. Subsequently, the aldolase is produced and accumulated in a medium and/or the cells by cultivating the transformants in the medium.

Thereafter, the purified aldolase is produced by recovering and purifying the enzyme.

The optically active IHOG may be produced on a large scale by using the purified aldolase, or the medium and/or the cells in which the aldolase has accumulated, for the aldol reaction.

The DNA molecule ligated to the vector DNA may be capable of expressing the aldolase of the present invention.

As an aldolase gene ligated to the vector DNA, any of the DNA molecules described in the above section "(2) Aldolase (i) DNA which encodes the aldolase" may be used.

When producing a protein on a large scale using recombinant DNA technology, a preferable mode thereof may include formation of an inclusion body of the protein. The advantages of this expression method include protection of the objective protein from digestion by proteases present in the bacterial cells, and ready purification of the objective protein by disruption of the bacterial cells, followed by centrifugation.

The protein inclusion body obtained in this manner may be solubilized by a protein denaturing agent, which is then subjected to activation regeneration mainly by eliminating the denaturing agent, thus restoring the correctly refolded and physiologically active protein. There are many examples of such procedures, such as activity regeneration of human interleukin 2 (JP 61-257931 A).

In order to obtain the active protein from the protein inclusion body, a series of the manipulations such as solubilization and activity regeneration is required, and thus the manipulation is more complicated than when the active protein is directly produced. However, when a protein that affects bacterial cell growth is produced on a large scale in bacterial cells, effects thereof may be suppressed by accumulating the protein as an inactive inclusion body in the bacterial cells.

The methods for producing the objective protein on a large scale may also include expressing the protein alone under the control of a strong promoter, as well as expressing the objective protein as a fusion protein with a protein that is known to be expressed in large amounts.

It is effective to arrange a recognition sequence of a restriction protease at an appropriate position to cleave out the objective protein after the fusion protein is expressed.

When the protein is produced on a large scale using recombinant DNA technology, the host cells to be transformed may include bacterial cells, actinomycetal cells, yeast cells, fungal cells, plant cells, or animal cells. The bacteria having a host-vector system may include genus *Escherichia*, genus *Pseudomonas*, genus *Corynebacterium*, and genus *Bacillus*, preferably *Escherichia coli* because there are many reported examples of producing proteins on a large scale using *Escherichia coli*. A method for producing the aldolase using transformed *Escherichia coli* (*E. coli*) will be described below.

As promoters for expressing the DNA, promoters which are usually used to produce foreign proteins in *E. coli* may be used, and examples thereof include strong promoters such as the T7 promoter, trp promoter, lac promoter, tac promoter, and PL promoter.

In order to produce the aldolase as a fusion protein inclusion body, a gene encoding another protein, preferably a hydrophilic peptide, is ligated either upstream or downstream from the aldolase gene. The gene encoding the other protein may increase the amount of the fusion protein that accumulates and enhance the solubility of the fusion protein, after modification and regeneration. Examples thereof include the T7 gene 10, β-galactosidase gene, dehydrofolate reductase gene, interferon γ gene, interleukin-2 gene, prochymosin gene, and the like.

The gene is ligated to the aldolase gene so that the reading frame match. This can be accomplished by using an appropriate restriction enzyme site for the ligation, or by using synthetic DNA with an appropriate sequence.

In order to increase the amount of the aldolase produced, it is preferable to ligate a terminator, i.e., a transcription termination sequence, downstream from the fusion protein gene. This terminator may include the T7 terminator, fd phage terminator, T4 terminator, the terminator of tetracycline resistant gene, and the terminator of *Escherichia coli* trpA gene.

As a vector to introduce DNA into *E. coli*, multi-copy vectors are preferable. Preferable plasmids include those having a replication origin derived from ColE1, such as pUC type plasmids, pBR322 type plasmids, or derivatives thereof. As used herein, the "derivatives" may include modifications which occur by substitution, deletion, insertion, addition, and/or inversion of nucleotides. The modification as referred to herein may also include modification by mutagens, UV irradiation, or spontaneous mutation.

It is preferred that the vector has a marker, such as an ampicillin resistant gene, for transformant selection. Expression vectors with strong promoters are commercially available pUC types (supplied from Takara Shuzo Co., Ltd.), pPROK types (supplied from Clontech), pKK233-2 (supplied from Clontech), and the like.

A recombinant DNA is obtained by ligating a DNA fragment so that the promoter, the aldolase gene or the DNA encoding the fusion protein, and the terminator are sequentially ligated, to the vector DNA.

E. coli is transformed using the recombinant DNA and this transformed E. coli is cultivated, thereby the aldolase or the fusion protein is expressed and produced. Bacteria which are typically used to express the foreign genes may be used, and in particular, E. coli JM109 (DE3) and JM109 strains are preferable. Methods for the transformation and for selecting the transformants are described in Molecular Cloning, 3rd edition, Cold Spring Harbor Press (2001).

When expressed as a fusion protein, the aldolase may be cleaved with a restriction protease which recognizes a sequence that is not present in the aldolase. The restriction protease includes blood coagulation factor Xa, kallikrein, or the like.

The production media may include media which is typically used for cultivating E. Coli, such as M9-casamino acid and LB medium. Culture conditions and production induction conditions may be appropriately selected depending on the type of vector, the promoter for the vector, the host bacteria, and the like.

The aldolase or the fusion protein may be harvested by solubilizing the bacterial cells, harvesting and then disrupting or lysing the cells, which results in a crude enzyme solution. If necessary, the aldolase or the fusion protein may be further purified using ordinary methods, such as precipitation, filtration, and column chromatography. In addition, purification utilizing an antibody against the aldolase or the fusion protein may also be used.

When a protein inclusion body is formed, solubilization with a denaturing agent may be performed. The inclusion body may be solubilized together with the bacterial cells. However, considering the following purification process, it is preferable to harvest the inclusion body before solubilization. Harvesting the inclusion body from the bacterial cells may be performed in accordance with conventionally and publicly known methods. For example, the bacterial cells are broken, and the inclusion body is recovered by centrifugation and the like. The denaturing agent that solubilizes the inclusion body of the protein may include guanidine-hydrochloric acid (e.g., 6 M, pH 5 to 8), urea (e.g., 8 M).

As a result of removing the denaturing agent by dialysis and the like, the protein may be regenerated so that it has activity. Dialysis solutions may include Tris hydrochloric acid buffer, phosphate buffer, and the like. The concentration thereof may be 20 mM to 0.5 M, and the pH thereof may be 5 to 8.

It is preferred that the protein concentration at the regeneration step is maintained at about 500 μg/ml or less. In order to inhibit self-crosslinking of the regenerated aldolase, the dialysis temperature is preferably 5° C. or lower. Methods for removing the denaturing agent may include dilution and ultrafiltration in addition to dialysis. The regeneration of the activity should occur using any of these methods.

When the DNA shown in SEQ ID NO:1 is used, the aldolase having the amino acid sequence according to SEQ ID NO:2 is produced.

(iii) Method for Culturing Bacterium Having Aldolase Activity

The culture method for bacteria that are a source of aldolase may be a liquid or solid culture, but a submerged culture with stirring and aeration is industrially advantageous. As nutrient sources in the medium, carbon sources, nitrogen sources, inorganic salts, and trace nutrient sources typically used for the cultivation of bacteria may be used. All may be used as long as they are compatible with the chosen strain.

An aerobic condition is employed as an aeration condition. The cultivation temperature may fall into the range where the bacteria grow and the aldolase is produced. Therefore, there is no strict condition, and the temperature is typically 10 to 50° C., preferably 30 to 40° C. The cultivation time varies depending on the other cultivation conditions. For example, cultivation may be performed until the aldolase is most abundantly produced, and typically for 5 hours to 7 days, and preferably for about 10 hours to 3 days.

(iv) Method for Isolating Aldolase from Bacteria

After the cultivation of the bacteria having the aldolase activity, bacterial cells are collected by centrifugation (e.g., 10,000×g, 10 min). Disrupting or lysing the bacterial cells can be used to solubilize the aldolase, since most of the aldolase is present in the bacterial cells. Processes such as ultrasonic disruption, French press disruption, or glass bead disruption may be employed to disrupt the bacterial cells. Treating with egg white lysozyme or peptidase or an appropriate combination thereof may be used to lyse the bacterial cells.

When the aldolase derived from aldolase-producing bacteria is purified, an enzyme solution may be used as the starting material. If undisrupted or unlysed cellular debris is present, it is desirable to remove the precipitated debris by centrifuging the solution again.

The aldolase may be purified by a standard method typically used when purifying enzymes, such as ammonium sulfate salting out, gel filtration chromatography, ion exchange chromatography, hydrophobic chromatography, and hydroxyapatite chromatography. As a result, a fraction containing the aldolase with higher specific activity may be obtained.

The amino acid sequence at the amino-terminus may be determined with a protein sequencer by Edman degradation (Edman, P., Acta Chem. Scand. 4, 227 (1950)). An internal amino acid sequence may be determined by preparing and purifying a peptide preparation by reverse phase HPLC subsequent to peptidase treatment, and applying it to the protein sequencer by Edman degradation.

Based on the known amino acid sequence, a nucleotide sequence of DNA encoding it may be deduced. The nucleotide sequence of the DNA may be deduced using universal codons.

Based on the deduced nucleotide sequence, a DNA molecule of about 30 base pairs is synthesized. A method for synthesizing DNA molecules is disclosed in Tetrahedron Letters, 22:1859 (1981). The DNA molecule may also be synthesized using a synthesizer supplied from Applied Biosystems. The DNA molecule may be utilized as a probe when the full length DNA encoding the aldolase is isolated from the chromosomal gene library of the aldolase-producing bacteria. Alternatively, the DNA molecule may be utilized as a primer when the DNA encoding the aldolase of the present invention is amplified by PCR. But, if the DNA amplified by PCR does not contain the full length DNA encoding the aldolase, the full length DNA encoding the aldolase can be isolated from the chromosomal gene library of the aldolase-producing bacteria.

The PCR procedure is described in White, T. J. et al., Trends Genet., 5:185 (1989). A method for preparing chromosomal DNA, and a method for isolating an objective DNA molecule from a gene library using a DNA molecule as a probe are described in Molecular Cloning, 3rd edition, Cold Spring Harbor press (2001).

A method for determining the nucleotide sequence of the isolated DNA encoding the aldolase is described in A Practical Guide to Molecular Cloning, John Wiley & Sons, Inc. (1985). Alternatively, a DNA sequencer (Applied Biosystems) can be used to determine the nucleotide sequence.

The DNA encoding the aldolase from the aldolase-producing bacteria may also be produced by obtaining a DNA probe which hybridizes with the full length or a partial sequence of the DNA encoding the aldolase of the present invention.

To obtain the DNA encoding the aldolase from the aldolase-producing bacteria, a sequence of a DNA probe may be deduced from a highly conserved region which can be determined by aligning the amino acid sequences, and the probe can be employed in PCR. When DNA amplified by PCR does not contain the full length DNA encoding the aldolase, the full length DNA encoding the aldolase is isolated from the chromosomal gene library of the aldolase-producing bacteria.

[II] Method for Producing Optically Active Monatin

Optically active monatin of the present invention may be produced by converting optically active IHOG produced as described in the section "[I] Method for producing optically active IHOG" to monatin. The IHOG produced in accordance with the method of the present invention is preferentially 4R-IHOG. Therefore, optically active 4R-monatin, i.e., (2R, 4R)-monatin and (2S, 4R)-monatin are preferentially produced from IHOG [(2R, 4R)-monatin and (2S, 4R)-monatin are collectively referred to as 4R-monatin].

The (2R, 4R)-monatin is the isomer with the highest sweetness of the 4 types of the monatin isomers. Therefore, it is preferable to use the 4R-isomer-rich IHOG when producing 4R-monatin. The percentage of 4R-IHOG of the total IHOG is preferably at least 55%, more preferably at least 60%, still more preferably at least 70%, and particularly preferably at least 80%.

A method for converting IHOG into monatin is not particularly limited, and a publicly known method, such as by chemical or enyzmatic reaction, may be used.

(1) Chemical Reaction Method

The method of producing monatin from IHOG is well described in previous publications, such as US Publication No. 2005-0004394 and 2006-0003426. To produce optically active monatin from optically active IHOG using a chemical reaction, optically active IHOG is oximated, and the corresponding IHOG-oxime shown in the following formula (4) or a salt thereof is chemically reduced to produce optically active monatin.

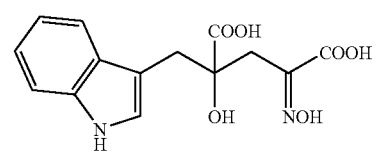

Preferably, 4R-isomer-rich IHOG is oximated, 4R-IHOG-oxime or the salt thereof is isolated by crystallizing a solution containing the 4R-isomer-rich IHOG, and the 4R-IHOG-oxime or the salt thereof is chemically reduced to produce 4R-monatin.

IHOG is oximated by reacting IHOG under neutral or alkali conditions with an amine compound represented by the following formula (3):

wherein R represents a hydrogen atom, an alkyl group, an aryl group, or an aralkyl group, or a salt thereof. When R is the alkyl, aryl, or aralkyl group, R is preferably the alkyl group having 1 to 3 carbon atoms, the aryl, or aralkyl group which may have a substituent on a side chain, and R is more preferably selected from a methyl, ethyl, or benzyl group in terms of crystallization.

This oximation reaction may be performed by directly adding the amine of formula (3) to an aldolase reaction mixture containing IHOG. The 4R-isomer may be isolated by crystallizing 4R-IHOG-oxime or the salt thereof from the solution containing the 4R-isomer-rich IHOG-oxime. A preferable crystallization solvent is water, an alcohol solvent, or an aqueous alcohol solvent.

4R-monatin may be obtained by reducing the 4R-IHOG-oxime or the salt thereof obtained by crystallization. 4R-IHOG-oxime or the salt thereof is reduced in the presence of hydrogen and a hydrogenated catalyst. As the hydrogenated catalyst, a metal catalyst such as platinum, rhodium, palladium, nickel, and cobalt is supported on a carrier such as silica, alumina, titania, magnesia, zirconia, and active charcoal.

Conventionally, optically active IHOG could not be efficiently produced. Therefore, to isolate 4R-IHOG from the racemate of IHOG (4R, 4S-IHOG), it was necessary to oximate 4R, 4S-IHOG, then subsequently react this with a chiral amine, and crystallize 4R-IHOG-oxime. On the contrary, in accordance with the present invention, 4R-isomer-rich IHOG can be produced by aldol condensation. Therefore, it is not necessary to optically resolute using the chiral amine before crystallization, and after the oximation of 4R-isomer-rich IHOG, 4R-IHOG-oxime may be directly crystallized. Thus, it becomes possible to decrease the cost to purify 4R-IHOG.

4R-Monatin obtained by chemical reduction is a racemic mixture of (2R, 4R)-monatin and (2S, 4R)-monatin. In order to isolate (2R, 4R)-monatin, (2R, 4R)-monatin may be crystallized. Specifically, the method described in International Publication Pamphlet WO03/059865 may be used.

(2) Enzymatic Method

To produce 4R-monatin from 4R-IHOG using an enzymatic method, an enzyme which aminates the position 2 of 4R-IHOG may be used. An enzyme that catalyzes this reaction includes an aminotransferase that catalyzes an amino group transfer reaction in 4R-IHOG or a dehydrogenase that catalyzes a reductive amination reaction of 4R-IHOG. It is preferable to use the aminotransferase.

Specifically, the method described in International Publication Pamphlet WO03/056026, US2006-0003426 and US2006-0003411 may be used.

If the aminotransferase is used, 4R-monatin is produced by reacting 4R-IHOG in the presence of the aminotransferase and an amino group donor.

It is possible to use either L-aminotransferase or D-aminotransferase. When L-aminotransferase is used, 2S-monatin may be selectively produced by transferring an amino group of an L-amino acid to position 2 of IHOG. When the D-aminotransferase is used, 2R-monatin may be selectively produced by transferring an amino group of a D-amino acid to position 2 of IHOG. Therefore, to selectively produce (2R, 4R)-monatin with high sweetness, it is preferable to react 4R-IHOG with the D-aminotransferase.

To produce monatin using the aminotransferase, this reaction may be performed after the aldol condensation and isolation of 4R-IHOG, or may be performed with the aldolase and the aminotransferase coexisting in the same solution. When the reactions are performed in the same solution, a bacteria which co-expresses the aldolase gene and the DNA encoding the aminotransferase may be used, or the enzymes may be prepared separately and added to the reaction solution. The bacteria (host cell) that co-expresses the aldolase gene and the DNA encoding the aminotransferase may be prepared by co-transfection of an expression vector containing the aldolase gene and an expression vector containing DNA which encodes the aminotransferase, or transforming the host cell with an expression vector which contains the DNA encoding the aldolase and the DNA encoding the aminotransferase.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

The present invention will be specifically described with reference to the following Examples, but the invention is not limited to these Examples. IHOG, PHOG, and (2R, 4R)-monatin were synthesized by methods according to Reference Examples 1, 2 and 3.

In the present Examples, IHOG and PHOG were quantified by HPLC analysis using "Inertsil ODS-2" (5 µm, 4.6×250 mm) supplied from GL Sciences Inc. The analysis conditions were as follows.

Mobile phase: 40% (v/v) acetonitrile/5 mM tetrabutylammonium dihydrogen phosphate solution
Flow rate: 1 mL/min
Column temperature: 40° C.
Detection: UV 210 nm Asymmetry of produced IHOG or PHOG was analyzed by HPLC analysis where "Inertsil ODS-2" (5 µm, 4.6×160 mm) supplied from GL Sciences Inc was directly connected with "SUMICHIRAL OA-7100" (5 µm, 4.6×250 mm) supplied from Sumika Chemical Analysis Service Ltd in this order. The analysis condition is as follows.

Mobile phase A: 5% (v/v) acetonitrile, 20 mM potassium phosphate buffer (pH 6.8)
Mobile phase B: 50% (v/v) acetonitrile, 20 mM potassium phosphate buffer (pH 6.8)
Eluted with the mobile phase A from 0 to 90 min, and from 90 to 20 min and washed with the mobile phase B.
Flow rate: 0.4 mL/min
Column temperature: 17° C.
Detection: UV 210 nm Example 1

Cloning of the IHOG Aldolase Gene Derived from *Escherichia coli* JM109 Strain (1) Preparation of Chromosomal DNA

*Escherichia coli* JM109 strain was cultivated using 50 ml of CM2G medium at 30° C. overnight (pre-cultivation). The main cultivation was performed using 5 ml of this culture as an inoculum and using 50 ml of the medium. After a late logarithmic growth phase, 50 ml of the culture was subjected to centrifugation (12,000 g, 4° C., 15 min) to harvest cells. Using these bacterial cells, chromosomal DNA was prepared in accordance with standard methods.

(2) Construction of IHOG Aldolase Gene-Expressing Plasmid ptrpgarL and Expression Thereof in *E. coli*

A fragment was obtained by amplifying the chromosomal DNA of *Escherichia coli* JM109 strain using primers (SEQ ID NOS: 3 and 4), and this fragment was digested with NdeI/PstI, and inserted into the NdeI/PstI site of pTrp4 to construct a plasmid ptrpgarL. This plasmid expresses the aldolase gene encoding the amino acid sequence of SEQ ID NO:2. Translation occurs from the translation initiation codon ATG at position 1 to the 771 th position in the nucleotide sequence of SEQ ID NO:1.

Example 2

Oximation of the Aldol Reaction Mixture and Isolation of 4R-IHOG-oxime

One platinum loop of *E. coli*/ptrpgarL cultivated on a LB-amp agar plate at 37° C. for 16 hours was inoculated into 500 mL flasks containing 50 ml of the LB-amp medium. Then, the shaking culture was conducted at 37° C. for 16 hours. Bacterial cells were harvested from the obtained 10 ml culture by centrifugation, suspended in and washed with buffer A (100 mM KPB, 100 mM Borate buffer, 10 g/dl Glycerol, 1 mM $MgCl_2$, (adjusted to pH 9.0 with KOH)), and centrifuged again to recover the cells. Bacterial cells collected by centrifugation were suspended in 1 mL of a reaction mixture of the following composition.

IHOG synthetic reaction mixture: 100 mM KPB, 100 mM Borate buffer, 300 mM indole pyruvic acid, 600 mM pyruvic acid sodium salt, 10 g/dl Glycerol, 1 mM $MgCl_2$ (adjusted to pH 9.0 with 6N KOH)

The reaction mixture in which the bacterial cells had been suspended was bubbled with the argon gas, and thereafter the reaction was performed under an argon gas atmosphere. The reaction was performed with stirring at 42° C. for 13 hours. After the completion of the reaction, about 1 mL of the aldol reaction mixture was obtained by centrifuging to remove the bacterial cells.

As the pH value was maintained at 9 with an aqueous solution of 6N sodium hydroxide, 2 mg (0.029 mmol) of hydroxylamine hydrochloride was added to about 0.02 mL of the aldol reaction mixture, which was then incubated at 25C for 6 hours. The amount of IHOG-oxime in the reaction mixture was quantitatively determined by HPLC analysis. As a result (Table 2), 4R-IHOG-oxime was preferentially produced.

TABLE 2

| | 4R-IHOG (mM) | 4S-IHOG (mM) | 4R yield (%) | 4R e.e. (%) |
|---|---|---|---|---|
| ptrpgarL | 57.6 | 7.8 | 19.2 | 76.2 |

Example 3

Production of 4R-monatin by Chemical Reduction of 4R-IHOG-oxime

The pH value of the obtained reaction mixture is adjusted to 2 using concentrated hydrochloric acid, and organic matters are extracted with ethyl acetate. An organic layer is concentrated to yield residue. To the residue, 12 mL of 28% aqueous ammonia and 25 mL of water are added, and crystallization is performed by adding 2-propanol to yield a crystal of diammonium salt of 4-hydroxy-4-(3-indolylmethyl)-2-hydroxyiminoglutaric acid. The crystal is dissolved in 60 mL of water, then 50 mL of 2-propanol is added at 50° C., and further 150 mL of 2-propanol is dripped over 3 hours at 50° C. Then, IHOG-oxime diammonium salt is obtained by filtering the crystal and drying it under reduced pressure. The asymmetry at position 4 of the crystal can be analyzed. Thus, 4R-IHOG-oxime ammonium salt with high purity can be isolated by crystallizing from 2-propanol.

5 g of the ammonium salt of (4R)-4-hydroxy-4-(3-indolylmethyl)-2-hydroxyiminoglutaric acid is dissolved in 60 mL of 28% aqueous ammonia, then 2.84 g of 5% rhodium carbon (50% hydrate product) is added thereto, and the reaction is conducted at room temperature under a hydrogen pressure of 1 MPa. After 17 hours, a catalyst is filtered out (0.2 μm filter), and 1.04 g (7.5 mmol) of potassium carbonate is dissolved in the filtrate. The dissolved solution is concentrated, and 20 mL of ethanol is added to the concentrate, which is then stirred at 25° C. 30 mL of ethanol is then dripped thereto over 3 hours, which is then stirred at 25° C. for 17 hours.

The resulting wet crystal is dissolved in 4 mL of water, and 8 mL of ethanol is added at 35° C., and then 17 mL of ethanol is dripped over 3 hours at 35° C. This resulting ethanol solution is cooled to 10° C. over 4 hours, and stirred at 10° C. for one hour. The resulting wet crystal is dried under reduced pressure to yield (2R, 4R)-monatin K salt. The optical purity of the monatin can be calculated.

Example 4

Purification of Recombinant Aldolase Enzyme

Recombinant aldolase is purified from a soluble fraction of *E. coli* to obtain high expression of the aldolase as follows. The aldolase activity is measured as the aldole cleavage activity using PHOG as the substrate under the following conditions.

Reaction conditions: 50 mM Hepes-KOH (pH 8.5), 2 mM PHOG, 0.25 mM NAD, 1 mM $MgCl_2$, 16 U/mL lactate dehydrogenase, 3 μL of enzyme per 600 μL of reaction mixture, 30° C., an absorbance at 340 nm is measured.

(1) Preparation of Soluble Fraction

One platinum loop of transformed *E. Coli* cultivated on a LB-amp agar plate at 37° C. for 16 hours is inoculated into 10 of 500 mL flasks containing 50 mL of the LB-amp medium. Then, the shaking culture is conducted at 37° C. for 16 hours. Bacterial cells are harvested from the culture by the centrifugation, suspended in and washed with the buffer A (20 mM Hepes-KOH, pH 7.6), and subsequently centrifuged again to collect the bacterial cells. The washed bacterial cells are suspended in 20 mL of the buffer A, and disrupted ultrasonically at 4° C. for 30 min. Bacterial cellular debris is removed by centrifuging a disruption suspension (×8000 rpm, 10 min, twice), and the resulting supernatant can be used as a crude extraction fraction.

(2) Anion Exchange Chromatography: Q-Sepharose FF

The crude extraction fraction (20 mL) obtained above is applied to an anion exchange chromatography column Q-Sepharose FF 26/10 (supplied from Pharmacia, CV=20 mL) pre-equilibrated with buffer A. Proteins that do not absorb to the column (unabsorbed proteins) are washed out with buffer A. Subsequently, the absorbed proteins are eluted with a linear gradient of a KCl concentration from 0 M to 0.7 M (total 140 mL). A PHOG aldolase activity is measured for each eluted fraction, and consequently a peak of the PHOG aldolase activity is detected in the fraction corresponding to about 0.4 M.

(3) Hydrophobic Chromatography: Phenyl Sepharose HP HR 16/10

The solution in which the aldolase activity is detected is dialyzed against buffer B (20 mM Hepes-KOH, 1 M ammonium sulfate, pH 7.6) at 4° C. overnight, and filtered through a filter with a pore size of 0.45 μm. The obtained filtrate is applied on a hydrophobic chromatography column, Phenyl Sepharose HP HR 16/10 (supplied from Pharmacia) pre-equilibrated with buffer B. This procedure allows the aldolase to absorb to the column.

Unabsorbed proteins are washed out with buffer B, and then the aldolase is eluted with a linear gradient of ammonium sulfate from 1 M to 0 M. The aldolase activity is measured for each eluted fraction, and the aldolase activity is detected in eluates where the concentration of ammonium sulfate is about 0.4 to 0.5 M.

(4) Gel Filtration Chromatography: Sephadex 200 HP 16/60

Fractions containing the aldolase are dialyzed against buffer A, and filtered through the filter with a pore size of 45 μm. The filtrate is concentrated using an ultrafiltration membrane, centriprep 10. The obtained concentrated solution is applied to a gel filtration Sephadex 200 HP 16/60 (supplied from Pharmacia) pre-equilibrated with buffer C (20 mM Hepes-KOH, 0.1 M KCl, pH 7.6), and eluted at a flow rate of 1 mL/min. This procedure allows the aldolase to elute in fractions of about 66 mL.

(5) Anion Exchange Chromatography: Mono Q HR 5/5

The fraction is filtered through a filter with a pore size of 0.45 μm. The filtrate is applied to an anion exchange chromatography column Mono-Q HR 5/5 (supplied from Pharmacia) pre-equilibrated with buffer A. This procedure allows the aldolase to absorb to the column. Unabsorbed proteins are washed out with buffer A, and subsequently the protein is eluted with a linear gradient of KCl from 0 mM to 700 mM (total 24 mL). The aldolase activity can be measured for each fraction.

The fractions purified by the above column chromatography can be subjected to SDS-PAGE to confirm which fraction contains recombinant aldolase, which may be detected by CBB staining resulting in a protein band. The obtained solution of the recombinant aldolase is dialyzed against buffer A at 4° C. overnight to obtain the solution containing aldolase.

Reference Example 1

Synthesis of
4-hydroxy-4-(3-indolylmethyl)-2-ketoglutaric acid
(IHOG)

Indole-3-pyruvic acid (7.50 g, 35.8 mmol, content 97.0% by weight) and 14.18 (107.4 mmol) g of oxaloacetic acid were added and dissolved in 64.45 mL of water in which 18.91 g (286.5 mmol, content 85% by weight) had been dissolved. This mixed solution was stirred at 35° C. for 24 hours.

40.0 mL of 3N hydrochloric acid was added to neutralize (pH 7.0), and 153.5 g of a neutralized reaction mixture was obtained. In this neutralized mixture, 5.55 g of 4-hydroxy-4-(3-indolylmethyl)-2-ketoglutaric acid was contained, and the yield (versus indole pyruvic acid) was 53.3%.

Water was added to this neutralized mixture to make 168 mL, which was then passed through a resin column filled with 840 mL of a synthetic absorbent (DIAION-SP207, supplied from Mitsubishi Chemical Corporation). An aqueous solution containing 3.04 g of 4-hydroxy-4-(3-indolylmethyl)-2-ketoglutaric acid with high purity was obtained by passing purified water at a flow rate of 23.5 mL per min and collecting 1.73 to 2.55 (L/L-R), and the yield (versus an applied amount onto the resin) was 54.7%.

(NMR Measurement)
$^1$H-NMR (400 MHz, $D_2O$): 3.03 (d, 1H, J=14.6 Hz), 3.11 (d, H, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz).
$^{13}$C-NMR (100 MHz, $D_2O$): 35.43, 47.91, 77.28, 109.49, 112.05, 119.44, 119.67, 121.91, 125.42, 128.41, 136.21, 169.78, 181.43, 203.58

Reference Example 2

Synthesis of
4-phenylmethyl-4-hydroxy-2-ketoglutaric acid
(PHOG)

Phenyl pyruvic acid (5.0 g, 30.5 mmol) and 12.1 g (91.4 mmol) of oxaloacetic acid were added to 25 mL of aqueous solution in which 13.8 g of potassium hydroxide (purity 85%) had been dissolved, and reacted at room temperature for 72 hours. The pH value of the reaction mixture was adjusted to 2.2 using concentrated hydrochloric acid, and the reaction mixture was extracted with ethyl acetate. An organic layer was washed with saturated aqueous NaCl solution, dried on magnesium sulfate anhydrate, and then concentrated. The concentrated residue was recrystallized from ethyl acetate and toluene to yield 2.8 g (11.3 mmol) of 4-phenylmethyl-4-hydroxy-2-ketoglutaric acid as crystal.

(NMR Measurement)
$^1$H NMR ($D_2O$) δ: 2.48(d, J=14.4 Hz, 0.18H), 2.60 (d, J=14.4 Hz, 0.18H), 2.85-3.30 (m, 3.64H), 7.17-7.36 (m, 5H)

(Molecular Weight Measurement)
ESI-MS Calculated value $C_{12}H_{12}O_6$=252.23, Analyzed value 251.22 (MH$^-$)

Reference Example 3

Production of 4-hydroxy-4-(3-indolylmethyl)-2-hydroxyiminoglutaric acid

Indole-3-pyruvic acid (73.8 g, 352 mmol) was added to and dissolved in 917 g of an aqueous solution of 1.6 wt % sodium hydroxide. The temperature of the reaction mixture was maintained at 35° C. As the pH value was maintained at 1.1 using an aqueous solution of 30% sodium hydroxide, 310.2 g (1761 mmol) of an aqueous solution of 50% pyruvic acid was dripped over 2 hours. The reaction was further continued for 4.5 hours to yield a reaction mixture containing 4-hydroxy-4-(3-indolylmethyl)-2-ketoglutaric acid. As the pH value was maintained at 7 with the addition of the aqueous solution of 30% sodium hydroxide, 367.2 g (2114 mmol) of an aqueous solution of 40% hydroxylamine hydrochloride was added thereto, and stirred at 5° C. for 17.5 hours. The pH value of the reaction mixture was adjusted to 2 using concentrated hydrochloric acid, and organic matters were extracted with ethyl acetate. The organic layer was washed with saturated aqueous NaCl solution, and concentrated to yield residue. The residue was recrystallized from 60 mL of 28% aqueous ammonia and 350 mL of 2-propanol to yield 43.4 g of diammonium salt of 4-hydroxy-4-(3-indolylmethyl)-2-hydroxyiminoglutaric acid (142 mmol, yield 40% versus indole-3-pyruvic acid) as crystal.

Reference Example 4

Production of (R)-(+)-1-phenylethylamine salt of (4S)-4-hydroxy-4-(3-indolylmethyl)-2-hydroxyiminoglutaric acid Ammonium salt (44.7 g, 0.131 mol) of 4-hydroxy-4-(3-indolylmethyl)-2-hydroxyiminoglutaric acid was dissolved in 500 mL of water at 25° C., and subsequently the pH value of the aqueous solution was adjusted to 2 with 25.5 g of 36% hydrochloric acid. The acidic solution was subjected to extraction with 1300 mL of ethyl acetate, and the ethyl acetate solution was washed with 200 mL of saturated aqueous NaCl solution. An aqueous solution (500 mL) of sodium carbonate (13.9 g, 0.131 mol) was added to the resulting ethyl acetate solution, and stirred to separate an alkali aqueous solution from ethyl acetate. The pH value of the resulting alkali aqueous solution was adjusted to 2 by adding 23.1 g of 36% hydrochloric acid. (R)-(+)-1-Phenylethylamine (6.99 g, 57.6 mmol) was dripped into the resulting acidic aqueous solution, and stirred at 25° C. for one hour. The yielded crystal was filtered, and dried under reduced pressure to yield 21.8 g (47.8 mmol) of (R)-(+)-1-phenylethylamine salt of (4S)-4-hydroxy-4-(3-indolylmethyl)-2-hydroxyiminoglutaric acid (yield: 72.7%, optical purity: 87.4%).

(NMR Measurement)

$^1$H-NMR (400 MHz, DMSO-d$_6$)δ:1.48(d, 3H, J=6.8 Hz), 2.63 (d, 1H, J=14.0 Hz), 2.70 (d, 1H, J=14.0 Hz), 2.90 (d, 1H, J=14.1 Hz), 3.06 (d, 1H, J=14.1 Hz), 4.40 (q, 1H, J=6.8 Hz), 6.91-7.54 (m, 10H)

Reference Example 5

Production of (S)-(−)-1-phenylethylamine salt of (4R)-4-hydroxy-4-(3-indolylmethyl)-2-hydroxyiminoglutaric acid (S)-(−)-1-Phenylethylamine (7.12 g, 58.7 mmol) was further dripped in the crystal filtrate obtained in Reference Example 4, and stirred at 25° C. for one hour. The crystal was filtered, and dried under reduced pressure to yield 23.8 g (53.3 mol) of (S)-(−)-1-phenylethylamine salt of (4R)-4-hydroxy-4-(3-indolylmethyl)-2-hydroxyiminoglutaric acid (yield: 81.1%. 1%, optical purity: 92.1%).

Reference Example 6

(1) Production of ammonium salt of (4S)-4-hydroxy-4-(3-indolylmethyl)-2-hydroxyiminoglutaric acid At 25° C., 21.8 g (51.0 mmol) of (R)-(+)-1-phenylethylamine salt of (4S)-4-hydroxy-4-(3-indolylmethyl)-2-hydroxyiminoglutaric acid was added to 200 mL of water and 18.5 g of 28% aqueous ammonia, and dissolved therein, and then 200 mL of toluene was added thereto and stirred. An aqueous layer obtained by separating the layers was heated to 60° C., and 900 mL of 2-propanol was dripped thereto over 2 hours. This 2-propanol aqueous solution was cooled to 10° C. over 5 hours, and then stirred at 10° C. for 10 hours. The yielded crystal was filtered, and dried under reduced pressure to yield 14.75 g of ammonium salt of (4S)-4-hydroxy-4-(3-indolylmethyl)-2-hydroxyiminoglutaric acid (yield: 85.1%, optical purity: 99.0%).

Melting point: 205° C. (degradation)

Specific optical rotation: $[\alpha]^2_D$+13.4 (c=1.00, H$_2$O)

(2) Production of ammonium salt of (4R)-4-hydroxy-4-(3-indolylmethyl)-2-hydroxyiminoglutaric acid In the same way as in the aforementioned Reference Example, 16.2 g of ammonium salt of (4R)-4-hydroxy-4-(3-indolylmethyl)-2-hydroxyiminoglutaric acid (yield: 89.3%, optical purity: 99.9%) was obtained from 23.8 g (53.3 mmol) of (R)-(+)-1-phenylethylamine salt of (4R)-4-hydroxy-4-(3-indolylmethyl)-2-hydroxyiminoglutaric acid.

Specific optical rotation: $[\alpha]^2_D$−13.6 (c=1.00, H$_2$O)

Reference Example 7

Production of (2R, 4R)-monatin

The ammonium salt of (4R)-4-hydroxy-4-(3-indolylmethyl)-2-hydroxyiminoglutaric acid (13.2 g, 38.7 mmol) obtained in Reference Example 6 was dissolved in 135 mL of 28% aqueous ammonia, 6.93 g of 5% rhodium carbon (50% aqueous article) was added, and the reaction was performed at 25° C. under hydrogen pressure of 1 MPa. After 24 hours, a catalyst was filtered out (0.2 μm filter), and 2.54 g (18.4 mmol) of potassium carbonate was dissolved in the filtrate. The dissolved solution was concentrated, 20 mL of water and 45 mL of ethanol were added to 32.7 g of the concentrate, and stirred at 25° C. 60 mL of ethanol was dripped over 3 hours, and then crystallization was conducted by stirring at 25° C. for 20 hours. The obtained wet crystal (9.78 g) was dissolved in 12 mL of water, 24 mL of ethanol was added, and then 51 mL of ethanol was dripped over 3 hours. This ethanol solution was cooled to 15° C. over 4 hours, and then stirred at 15° C. for 10 hours. The yielded wet crystal (7.08 g) was dried under reduced pressure to give 5.7 g of the objective potassium salt of (2R, 4R)-monatin.

As described in the above, by the use of the aldolase of the present invention, it becomes possible to produce IHOG and PHOG with optical selectivity. The aldolase of the present invention enables efficient introduction of the asymmetry in the aldol condensation reaction in the synthetic route of monatin, and may be used for the production of optically active IHOG and monatin.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents. All of the cited documents herein are hereby incorporated by reference.

The invention claimed is:

1. A method for producing (4R)-4-(indole-3-ylmethyl)-4-hydroxy-2-oxoglutaric acid (4R-IHOG) of formula (1) or a salt thereof:

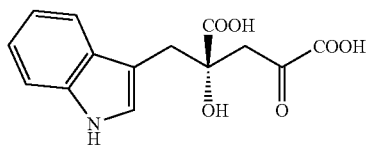

(1)

comprising
A) reacting indole-3-pyruvic acid with pyruvic acid or oxaloacetic acid in the presence of an aldolase to produce 4R-IHOG, wherein said aldolase is selected from the group consisting of:
(a) a protein comprising the amino acid sequence of SEQ ID NO:2,
(b) a protein that is at least 95% homologous to the amino acid sequence in SEQ ID NO:2 and wherein the protein has 4R-aldolase activity,
(d) a protein encoded by a DNA comprising the nucleic acid sequence of SEQ ID NO: 1, and
(e) a protein encoded by a DNA that hybridizes under stringent conditions of 0.1×SSC and 0.1% SDS at 65° C. with a DNA having a nucleotide sequence complementary to the nucleotide sequence of SEQ ID No: 1, and wherein the DNA encodes a protein having 4R-aldolase activity.

2. The method according to claim 1, wherein said aldolase is obtained from a bacteria belonging to the genus *Escherichia*.

3. The method according to claim 2, wherein the bacteria is *Escherichia coli*.

4. A method for producing 4R-monatin or a salt thereof comprising:
reacting indole-3-pyruvic acid with pyruvic acid or oxaloacetic acid in the presence of an aldolase to preferentially produce 4R-IHOG, wherein said aldolase is selected from the group consisting of:
(a) a protein comprising the amino acid sequence of SEQ ID NO:2, and
(b) a protein that is at least 95% homologous to the amino acid sequence of SEQ ID NO:2 and wherein the protein has 4R-aldolase activity, and
converting a carbonyl group of 4R-IHOG, or the salt thereof, to an amino group to produce 4R-monatin, or the salt thereof, of formula (2),

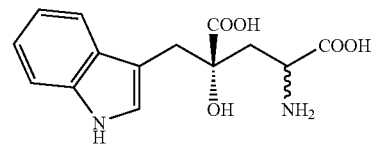

(2)

wherein a wavy line represents a bond wherein both R- and S-configurations are included.

5. The method according to claim 4, wherein said converting is by amination by an enzyme of said carbonyl group to an amino group, and wherein the enzyme is an aminotransferase.

6. The method according to claim 4, wherein said converting comprises reacting 4-(indole-3-ylmethyl)-4-hydroxy-2-oxoglutaric acid with an amine compound or a salt thereof of formula (3):

$$H_2N-O-R \quad (3)$$

wherein R represents a hydrogen atom, an alkyl, an aryl, or an aralkyl group, under neutral or alkali conditions to produce 4-hydroxy-4-(3-indolylmethyl)-2-hydroxyiminoglutaric acid (IHOG-oxime) or the salt thereof of formula (4):

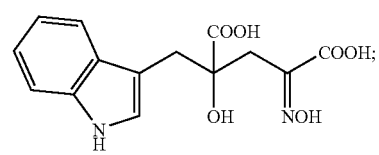

(4)

and crystallizing the 4R-isomer of the IHOG-oxime or the salt thereof; and reducing the crystallized 4R-isomer to produce 4R-monatin or the salt thereof.

7. The method according to claim 6, wherein the amine compound of formula (3) is selected from the group consisting of hydroxylamine, methoxyamine, benzyloxyamine, and combinations thereof.

8. The method according to claim 6, wherein the 4R-isomer of IHOG-oxime or the salt thereof is reduced in the presence of hydrogen and a hydrogenated catalyst.

9. The method according to claim 6, wherein (2R, 4R)-monatin is recovered by said crystallizing.

10. The method ac cording to claim 6, wherein said crystallizing is performed with a crystallization solvent selected from the group consisting of water, an alcohol solvent, and an aqueous alcohol solvent.

11. The method according to claim 1, wherein the aldolase is present within a bacterial cell or treated bacterial cells, and said cell or cells are modified to increase expression of the aldolase as compared to a non-modified cell or cells, wherein the cell or cells are modified by a method selected from the group consisting of:
   a) modifying an expression control sequence of the gene encoding the aldolase,
   b) increasing the copy number of the gene encoding the aldolase, and
   c) combinations thereof.

12. The method according to claim 11, wherein the expression of the aldolase is increased by increasing the expression of garL.

13. The method according to claim 12, wherein the expression of the aldolase is increased by modifying an expression control sequence of the gene encoding the aldolase or by increasing the copy number of the garL gene.

14. The method according to claim 13, wherein the gene encoding the aldolase is selected from the group consisting of:
   (i) A DNA comprising the nucleic acid sequence of SEQ ID NO: 1,
   (ii) A DNA that hybridizes under stringent conditions of 0.1×SSC and 0.1% SDS at 65° C. with a DNA having a nucleotide sequence complementary to the nucleotide sequence of SEQ ID No: 1 and wherein said DNA encodes a protein having 4R-aldolase activity,
   (iii) A DNA that encodes a protein comprising the amino acid sequence of SEQ ID No: 2, and
   (iv) A DNA that encodes a protein having an amino acid sequence that is at least 95% homologous to the amino acid sequence of SEQ ID NO: 2 and wherein said protein has aldolase activity.

15. The method according to claim 4, wherein said protein is obtained from a bacteria belonging to the genus *Escherichia*.

16. The met hod according to claim 15, wherein the bacteria is *Escherichia coli*.

17. A method for producing 4R-monatin or a salt thereof comprising:
   reacting indole-3-pyruvic acid with pyruvic acid or oxaloacetic acid in the presence of an aldolase to preferentially produce 4R-IHOG, wherein said aldolase is selected from the group consisting of:
      (a) a protein comprising the amino acid sequence of SEQ ID NO:2, and
      (b) a protein that is at least 95% homologous to the amino acid sequence of SEQ ID NO:2 and wherein the protein has 4R-aldolase activity, and
   converting a carbonyl group of 4R-IHOG, or the salt thereof, to an amino group to produce 4R-monatin, or the salt thereof, of formula (2),

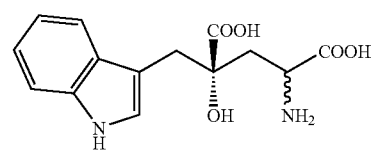

(2)

wherein a wavy line represents a bond wherein both R- and S-configurations are included,
   wherein said aldolase is present within a bacterial cell or treated bacterial cells, and said cell or cells are modified to increase expression of the aldolase as compared to a non-modified cell or cells, wherein the cell or cells are modified by a method selected from the group consisting of:
      a) modifying an expression control sequence of the gene encoding the aldolase,
      b) increasing the copy number of the gene encoding the aldolase, and
      c) combinations thereof.

18. The method according to claim 17, wherein the expression of the aldolase is increased by increasing the expression of garL.

19. The method according to claim 18, wherein the expression of the aldolase is increased by modifying an expression control sequence of the gene encoding the aldolase or by increasing the copy number of the garL gene.

20. The method according to claim 19, wherein the gene encoding the aldolase is selected from the group consisting of:
   (i) A DNA comprising the nucleic acid sequence of SEQ ID NO: 1,
   (ii) A DNA that hybridizes under stringent conditions of 0.1×SSC and 0.1% SDS at 65° C. with a DNA having a nucleotide sequence complementary to the nucleotide sequence of SEQ ID No: 1 and wherein said DNA encodes a protein having 4R-aldolase activity,
   (iii) A DNA that encodes a protein comprising the amino acid sequence of SEQ ID No: 2, and
   (iv) A DNA that encodes a protein having an amino acid sequence that is at least 95% homologous to the amino acid sequence of SEQ ID NO: 2 and wherein said protein has aldolase activity.

21. The method according to claim 17, wherein said protein is obtained from a bacteria belonging to the genus *Escherichia*.

22. The method according to claim 21, wherein the bacteria is *Escherichia coli*.

* * * * *

SEQUENCE LISTING

<160> NUMBER OF SEQ ID NOS: 10

<210> SEQ ID NO 1
<211> LENGTH: 771
<212> TYPE: DNA
<213> ORGANISM: Escherichia coli
<220> FEATURE:
<221> NAME/KEY: CDS
<222> LOCATION: (1)..(771)

<400> SEQUENCE: 1

```
atg aat aac gat gtt ttc ccg aat aaa ttc aaa gcc gca ctg gct gcg      48
Met Asn Asn Asp Val Phe Pro Asn Lys Phe Lys Ala Ala Leu Ala Ala
1               5                   10                  15
```

```
aaa cag gta caa att ggt tgc tgg tca gca ctc tct aac ccg att agc      96
Lys Gln Val Gln Ile Gly Cys Trp Ser Ala Leu Ser Asn Pro Ile Ser
             20                  25                  30 act gaa gtt ctt ggt ttg gct ggg ttt gac tgg ctg gtg ctg gat ggc     144
Thr Glu Val Leu Gly Leu Ala Gly Phe Asp Trp Leu Val Leu Asp Gly
         35                  40                  45 gaa cat gcg cca aac gat atc tcc acg ttt att ccg cag tta atg gcc     192
Glu His Ala Pro Asn Asp Ile Ser Thr Phe Ile Pro Gln Leu Met Ala
 50                  55                  60 ttg aaa ggc agc gcc agc gcg cca gta gtg cga gtg ccg acc aac gag     240
Leu Lys Gly Ser Ala Ser Ala Pro Val Val Arg Val Pro Thr Asn Glu
 65                  70                  75                  80 ccg gta att att aag cgt ctt ctg gat atc ggt ttc tat aac ttc ctg     288
Pro Val Ile Ile Lys Arg Leu Leu Asp Ile Gly Phe Tyr Asn Phe Leu
                 85                  90                  95 att cct ttt gta gaa aca aaa gag gaa gca gag ctg gcg gtg gca tca     336
Ile Pro Phe Val Glu Thr Lys Glu Glu Ala Glu Leu Ala Val Ala Ser
            100                 105                 110 acc cgt tac cca ccg gaa ggc att cgc ggc gtc tcc gtt tct cac cgc     384
Thr Arg Tyr Pro Pro Glu Gly Ile Arg Gly Val Ser Val Ser His Arg
        115                 120                 125 gcc aat atg ttt ggc acc gtg gcg gat tat ttc gct cag tcg aac aag     432
Ala Asn Met Phe Gly Thr Val Ala Asp Tyr Phe Ala Gln Ser Asn Lys
    130                 135                 140 aac atc act att ctg gtc cag ata gaa agt cag cag ggc gta gat aac     480
Asn Ile Thr Ile Leu Val Gln Ile Glu Ser Gln Gln Gly Val Asp Asn
145                 150                 155                 160 gtc gat gcc att gcc gct acc gaa ggc gta gac ggc atc ttc gtc ggc     528
Val Asp Ala Ile Ala Ala Thr Glu Gly Val Asp Gly Ile Phe Val Gly
                165                 170                 175 ccc agc gat ctg gcc gcg gca tta ggc cat ctc ggc aat gca tca cac     576
Pro Ser Asp Leu Ala Ala Ala Leu Gly His Leu Gly Asn Ala Ser His
            180                 185                 190 ccg gat gta caa aaa gca att cag cac att ttt aac cgt gcc agc gcg     624
Pro Asp Val Gln Lys Ala Ile Gln His Ile Phe Asn Arg Ala Ser Ala
        195                 200                 205 cac ggc aaa ccc agc ggt atc ctc gcg ccg gtc gaa gcc gat gcg cgt     672
His Gly Lys Pro Ser Gly Ile Leu Ala Pro Val Glu Ala Asp Ala Arg
    210                 215                 220 cgt tat ctg gaa tgg ggc gcg acg ttt gtg gct gtc ggc agc gat ctc     720
Arg Tyr Leu Glu Trp Gly Ala Thr Phe Val Ala Val Gly Ser Asp Leu
225                 230                 235                 240 ggc gtc ttc cgc tct gcc act cag aaa ctg gct gat acc ttt aaa aaa     768
Gly Val Phe Arg Ser Ala Thr Gln Lys Leu Ala Asp Thr Phe Lys Lys
                245                 250                 255 taa                                                                 771

<210> SEQ ID NO 2
<211> LENGTH: 256
<212> TYPE: PRT
<213> ORGANISM: Escherichia coli

<400> SEQUENCE: 2

Met Asn Asn Asp Val Phe Pro Asn Lys Phe Lys Ala Ala Leu Ala Ala
1               5                   10                  15

Lys Gln Val Gln Ile Gly Cys Trp Ser Ala Leu Ser Asn Pro Ile Ser
            20                  25                  30

Thr Glu Val Leu Gly Leu Ala Gly Phe Asp Trp Leu Val Leu Asp Gly
        35                  40                  45
```

```
Glu His Ala Pro Asn Asp Ile Ser Thr Phe Ile Pro Gln Leu Met Ala
     50                  55                  60

Leu Lys Gly Ser Ala Ser Ala Pro Val Val Arg Val Pro Thr Asn Glu
 65                  70                  75                  80

Pro Val Ile Ile Lys Arg Leu Leu Asp Ile Gly Phe Tyr Asn Phe Leu
                 85                  90                  95

Ile Pro Phe Val Glu Thr Lys Glu Glu Ala Glu Leu Ala Val Ala Ser
                100                 105                 110

Thr Arg Tyr Pro Pro Glu Gly Ile Arg Gly Val Ser Val Ser His Arg
                115                 120                 125

Ala Asn Met Phe Gly Thr Val Ala Asp Tyr Phe Ala Gln Ser Asn Lys
    130                 135                 140

Asn Ile Thr Ile Leu Val Gln Ile Glu Ser Gln Gln Gly Val Asp Asn
145                 150                 155                 160

Val Asp Ala Ile Ala Ala Thr Glu Gly Val Asp Gly Ile Phe Val Gly
                165                 170                 175

Pro Ser Asp Leu Ala Ala Ala Leu Gly His Leu Gly Asn Ala Ser His
                180                 185                 190

Pro Asp Val Gln Lys Ala Ile Gln His Ile Phe Asn Arg Ala Ser Ala
            195                 200                 205

His Gly Lys Pro Ser Gly Ile Leu Ala Pro Val Glu Ala Asp Ala Arg
    210                 215                 220

Arg Tyr Leu Glu Trp Gly Ala Thr Phe Val Ala Val Gly Ser Asp Leu
225                 230                 235                 240

Gly Val Phe Arg Ser Ala Thr Gln Lys Leu Ala Asp Thr Phe Lys Lys
                245                 250                 255
```

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
ggaattccat atgaataacg atgttttccc                                30

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
gcccaagctt ttattttta aaggtatcag                                 30

<210> SEQ ID NO 5
<211> LENGTH: 256
<212> TYPE: PRT
<213> ORGANISM: Artificial
<220> FEATURE:
<223> OTHER INFORMATION: core sequence
<220> FEATURE:
<221> NAME/KEY: MISC_FEATURE
<222> LOCATION: (1)..(256)
<223> OTHER INFORMATION: Xaa represents any amino acids.

<400> SEQUENCE: 5

Xaa Xaa Xaa Xaa Xaa Xaa Asn Lys Xaa Lys Xaa Xaa Xaa Ala Xaa Xaa

```
                 1               5                  10                 15
Xaa Val Xaa Xaa Gly Cys Trp Ser Ala Leu Ser Xaa Xaa Xaa Ser Xaa
                        20                  25                  30

Xaa Glu Val Leu Gly Leu Ala Gly Phe Asp Trp Leu Val Leu Asp Gly
            35                  40                  45

Glu His Ala Pro Asn Asp Xaa Xaa Thr Xaa Ile Pro Gln Leu Met Ala
         50                  55                  60

Leu Xaa Gly Ser Xaa Ser Ala Pro Val Val Arg Xaa Pro Xaa Asn Glu
65                  70                  75                  80

Pro Val Ile Ile Lys Arg Xaa Leu Asp Ile Gly Phe Tyr Asn Phe Leu
                     85                  90                  95

Ile Pro Phe Val Glu Xaa Xaa Glu Glu Ala Xaa Xaa Ala Val Ala Ser
                 100                 105                 110

Thr Arg Tyr Pro Pro Xaa Gly Ile Arg Gly Val Ser Val Ser His Arg
             115                 120                 125

Xaa Asn Xaa Xaa Gly Thr Val Xaa Asp Tyr Phe Ala Xaa Xaa Asn Xaa
         130                 135                 140

Asn Ile Thr Xaa Xaa Val Gln Ile Glu Ser Gln Xaa Gly Val Asp Asn
145                 150                 155                 160

Xaa Asp Ala Ile Ala Ala Xaa Glu Gly Val Asp Xaa Ile Phe Val Gly
                 165                 170                 175

Pro Xaa Asp Leu Xaa Ala Ala Leu Gly Xaa Leu Gly Xaa Xaa Xaa His
             180                 185                 190

Pro Xaa Val Gln Xaa Xaa Ile Xaa His Ile Phe Xaa Arg Ala Xaa Ala
         195                 200                 205

Xaa Gly Lys Pro Xaa Gly Ile Leu Ala Pro Val Xaa Ala Asp Ala Arg
     210                 215                 220

Arg Tyr Leu Xaa Trp Gly Ala Thr Phe Val Ala Val Gly Ser Asp Leu
225                 230                 235                 240

Gly Xaa Phe Arg Xaa Xaa Thr Gln Xaa Leu Xaa Asp Xaa Phe Lys Lys
                 245                 250                 255

<210> SEQ ID NO 6
<211> LENGTH: 256
<212> TYPE: PRT
<213> ORGANISM: Shigella sonnei

<400> SEQUENCE: 6

Met Asn Asn Asp Val Phe Pro Asn Lys Phe Lys Ala Ala Leu Ala Ala
1               5                   10                  15

Lys Gln Val Gln Ile Gly Cys Trp Ser Ala Leu Ser Asn Pro Ile Ser
            20                  25                  30

Thr Glu Val Leu Gly Leu Ala Gly Phe Asp Trp Leu Val Leu Asp Gly
        35                  40                  45

Glu His Ala Pro Asn Asp Ile Ser Thr Phe Ile Pro Gln Leu Met Ala
     50                  55                  60

Leu Lys Gly Ser Ala Ser Ala Pro Val Val Arg Val Pro Thr Asn Glu
65                  70                  75                  80

Pro Val Ile Ile Lys Arg Leu Leu Asp Ile Gly Phe Tyr Asn Phe Leu
                85                  90                  95

Ile Pro Phe Val Glu Thr Lys Glu Glu Ala Glu Gln Ala Val Ala Ser
            100                 105                 110

Thr Arg Tyr Pro Pro Glu Gly Ile Arg Gly Val Ser Val Ser His Arg
        115                 120                 125
```

```
Thr Asn Met Phe Gly Thr Val Ala Asp Tyr Phe Ala Gln Ser Asn Lys
            130                 135                 140

Asn Ile Thr Ile Leu Val Gln Ile Glu Ser Gln Gln Gly Val Asp Asn
145                 150                 155                 160

Val Asp Ala Ile Ala Ala Thr Glu Gly Val Asp Gly Ile Phe Val Gly
                165                 170                 175

Pro Ser Asp Leu Ala Ala Ala Leu Gly His Leu Gly Asn Ala Ser His
            180                 185                 190

Pro Asp Val Gln Lys Ala Ile Gln His Ile Phe Asn Arg Ala Ser Ala
            195                 200                 205

His Gly Lys Pro Ser Gly Ile Leu Ala Pro Val Glu Ala Asp Ala Arg
            210                 215                 220

Arg Tyr Leu Glu Trp Gly Ala Thr Phe Val Ala Val Gly Ser Asp Leu
225                 230                 235                 240

Gly Val Phe Arg Ser Ala Thr Gln Lys Leu Ala Asp Thr Phe Lys Lys
                245                 250                 255

<210> SEQ ID NO 7
<211> LENGTH: 256
<212> TYPE: PRT
<213> ORGANISM: Shigella dysenteriae

<400> SEQUENCE: 7

Met Asn Asn Asp Val Phe Pro Asn Lys Phe Lys Ala Ala Leu Ala Ala
1               5                   10                  15

Lys Gln Val Gln Ile Gly Cys Trp Ser Ala Leu Ser Asn Pro Ile Ser
            20                  25                  30

Thr Glu Val Leu Gly Leu Ala Gly Phe Asp Trp Leu Val Leu Asp Gly
            35                  40                  45

Glu His Ala Pro Asn Asp Ile Ser Thr Phe Ile Pro Gln Leu Met Ala
        50                  55                  60

Leu Lys Gly Ser Ala Ser Ala Pro Val Val Arg Val Pro Thr Asn Glu
65                  70                  75                  80

Pro Val Ile Ile Lys Arg Leu Leu Asp Ile Gly Phe Tyr Asn Phe Leu
                85                  90                  95

Ile Pro Phe Val Glu Thr Lys Glu Glu Ala Glu Gln Ala Val Ala Ser
            100                 105                 110

Thr Arg Tyr Pro Pro Glu Gly Ile Arg Gly Val Ser Val Ser His Arg
        115                 120                 125

Ala Asn Met Phe Gly Thr Val Ala Asp Tyr Phe Ala Gln Ser Asn Lys
            130                 135                 140

Asn Ile Thr Ile Leu Val Gln Ile Glu Ser Gln Gln Gly Val Asp Asn
145                 150                 155                 160

Val Asp Ala Ile Ala Ala Thr Glu Gly Val Asp Gly Ile Phe Val Gly
                165                 170                 175

Pro Ser Asp Leu Ala Ala Ala Leu Gly His Leu Gly Asn Ala Ser His
            180                 185                 190

Pro Asp Val Gln Lys Ala Ile Gln His Ile Phe Asn Arg Ala Ser Ala
            195                 200                 205

His Gly Lys Pro Ser Gly Ile Leu Ala Pro Val Glu Ala Asp Ala Arg
            210                 215                 220

Arg Tyr Leu Ala Trp Gly Ala Thr Phe Val Ala Val Gly Ser Asp Leu
225                 230                 235                 240

Gly Val Phe Arg Ser Ala Thr Gln Lys Leu Ala Asp Thr Phe Lys Lys
                245                 250                 255
```

<210> SEQ ID NO 8
<211> LENGTH: 257
<212> TYPE: PRT
<213> ORGANISM: Shigella boydii

<400> SEQUENCE: 8

Met Glu Ser Leu Pro Val Phe Pro Asn Lys Phe Lys Ala Ala Leu Ala
1               5                   10                  15

Ala Lys Gln Val Gln Ile Gly Cys Trp Ser Ala Leu Ser Asn Pro Ile
            20                  25                  30

Ser Thr Glu Val Leu Gly Leu Ala Gly Phe Asp Trp Leu Val Leu Asp
        35                  40                  45

Gly Glu His Ala Pro Asn Asp Ile Ser Thr Phe Ile Pro Gln Leu Met
    50                  55                  60

Ala Leu Lys Gly Ser Ala Ser Ala Pro Val Val Arg Val Pro Thr Asn
65                  70                  75                  80

Glu Pro Val Ile Ile Lys Arg Leu Leu Asp Ile Gly Phe Tyr Asn Phe
                85                  90                  95

Leu Ile Pro Phe Val Glu Thr Lys Glu Glu Ala Glu Gln Ala Val Ala
            100                 105                 110

Ser Thr Arg Tyr Pro Pro Glu Gly Ile Arg Gly Val Ser Val Ser His
        115                 120                 125

Arg Ala Asn Met Phe Gly Thr Val Ala Asp Tyr Phe Ala Gln Ser Asn
    130                 135                 140

Lys Asn Ile Thr Ile Leu Val Gln Ile Glu Ser Gln Gln Gly Val Asp
145                 150                 155                 160

Asn Val Asp Ala Ile Ala Ala Thr Glu Gly Val Asp Cys Ile Phe Val
                165                 170                 175

Gly Pro Ser Asp Leu Ala Ala Ala Leu Gly His Leu Gly Asn Ala Ser
            180                 185                 190

His Pro Asp Val Gln Lys Ala Ile Gln His Ile Phe Asn Arg Ala Ser
        195                 200                 205

Ala His Gly Lys Pro Ser Gly Ile Leu Ala Pro Val Glu Ala Asp Ala
    210                 215                 220

Arg Arg Tyr Leu Glu Trp Gly Ala Thr Phe Val Ala Val Gly Ser Asp
225                 230                 235                 240

Leu Gly Val Phe Arg Ser Ala Thr Gln Lys Leu Ala Asp Thr Phe Lys
                245                 250                 255

Lys

<210> SEQ ID NO 9
<211> LENGTH: 256
<212> TYPE: PRT
<213> ORGANISM: Salmonella enterica

<400> SEQUENCE: 9

Met Asn Asn Ala Ile Phe Pro Asn Lys Phe Lys Ala Ala Leu Ala Ala
1               5                   10                  15

Gln Gln Val Gln Ile Gly Cys Trp Ser Ala Leu Ala Ser Pro Ile Thr
            20                  25                  30

Thr Glu Val Leu Gly Leu Ala Gly Phe Asp Trp Leu Val Leu Asp Gly
        35                  40                  45

Glu His Ala Pro Asn Asp Val Ser Thr Leu Ile Pro Gln Leu Met Ala
    50                  55                  60

```
Leu Lys Gly Ser Ala Ser Ala Pro Val Val Arg Val Pro Thr Asn Glu
 65                  70                  75                  80

Pro Val Ile Ile Lys Arg Met Leu Asp Ile Gly Phe Tyr Asn Phe Leu
                 85                  90                  95

Ile Pro Phe Val Glu Thr Gln Glu Glu Ala Ala Arg Ala Val Ala Ser
            100                 105                 110

Thr Arg Tyr Pro Pro Glu Gly Ile Arg Gly Val Ser Val Ser His Arg
        115                 120                 125

Ala Asn Met Phe Gly Thr Val Pro Asp Tyr Phe Ala Gln Ser Asn Lys
130                 135                 140

Asn Ile Thr Ile Ile Val Gln Ile Glu Ser Gln Leu Gly Val Asp Asn
145                 150                 155                 160

Val Asp Ala Ile Ala Ala Thr Glu Gly Val Asp Gly Ile Phe Val Gly
                165                 170                 175

Pro Ser Asp Leu Ala Ala Ala Leu Gly His Leu Gly Asn Ala Ser His
            180                 185                 190

Pro Asp Val Gln Gln Thr Ile Gln His Ile Phe Ala Arg Ala Lys Ala
        195                 200                 205

His Gly Lys Pro Cys Gly Ile Leu Ala Pro Val Glu Ala Asp Ala Arg
210                 215                 220

Arg Tyr Leu Glu Trp Gly Ala Thr Phe Val Ala Val Gly Ser Asp Leu
225                 230                 235                 240

Gly Ala Phe Arg Ala Ser Thr Gln Lys Leu Ala Asp Thr Phe Lys Lys
                245                 250                 255
```

<210> SEQ ID NO 10
<211> LENGTH: 256
<212> TYPE: PRT
<213> ORGANISM: Yersinia mollaretii

<400> SEQUENCE: 10

```
Met Ser Leu Pro Asn Tyr Pro Asn Gln Phe Arg Arg Asn Leu Gln Gln
  1               5                  10                  15

Gly Gln Thr Leu Ile Gly Cys Trp Ser Ala Leu Ala Asn His Ile Ser
                 20                  25                  30

Ala Glu Val Leu Gly Leu Ala Gly Phe Asp Trp Leu Val Leu Asp Gly
             35                  40                  45

Glu His Ala Pro Asn Asp Val Thr Thr Phe Ile Pro Gln Leu Met Ala
         50                  55                  60

Leu Thr Gly Ser Gly Ser Ala Pro Val Val Arg Ala Pro Cys Asn Glu
 65                  70                  75                  80

Pro Val Ile Ile Lys Arg Leu Leu Asp Ile Gly Phe Tyr Asn Phe Leu
                 85                  90                  95

Ile Pro Phe Val Glu Ser Glu Glu Ala Ile Arg Ala Val Ala Ser
            100                 105                 110

Thr Arg Tyr Pro Pro Ala Gly Ile Arg Gly Val Ser Val Ser His Arg
        115                 120                 125

Gly Asn His Tyr Gly Thr Val Pro Asp Tyr Phe Ala Thr Ile Asn Asp
130                 135                 140

Asn Ile Thr Val Leu Val Gln Ile Glu Ser Gln Gln Gly Val Asp Asn
145                 150                 155                 160

Leu Asp Ala Ile Ala Ala Val Glu Gly Val Asp Gly Ile Phe Val Gly
                165                 170                 175

Pro Gly Asp Leu Ser Ala Ala Leu Gly Tyr Leu Gly Gln Pro Asn His
            180                 185                 190
```

-continued

```
Pro Glu Val Gln Lys Val Ile Arg His Ile Phe Asp Arg Ala Lys Ala
    195                 200                 205

Gln Gly Lys Pro Ser Gly Ile Leu Ala Pro Val Asp Ala Asp Ala Arg
    210             215                 220

Arg Tyr Leu Glu Trp Gly Ala Thr Phe Val Ala Val Gly Ser Asp Leu
225             230                 235                 240

Gly Val Phe Arg Ser Ala Thr Gln Ala Leu Cys Asp Lys Phe Lys Lys
                245             250                 255
```